US008748450B2

(12) United States Patent
Tung

(10) Patent No.: US 8,748,450 B2
(45) Date of Patent: *Jun. 10, 2014

(54) MORPHINAN COMPOUNDS

(71) Applicant: Concert Pharmaceuticals Inc., Lexington, MA (US)

(72) Inventor: Roger Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/949,499

(22) Filed: Jul. 24, 2013

(65) Prior Publication Data

US 2013/0310415 A1  Nov. 21, 2013

Related U.S. Application Data

(63) Continuation of application No. 13/118,935, filed on May 31, 2011, now Pat. No. 8,541,436, which is a continuation of application No. 12/112,936, filed on Apr. 30, 2008, now Pat. No. 7,973,049.

(60) Provisional application No. 60/976,044, filed on Sep. 28, 2007, provisional application No. 60/916,662, filed on May 8, 2007, provisional application No. 60/915,130, filed on May 1, 2007.

(51) Int. Cl.
*A61K 31/4748* (2006.01)
*C07D 221/28* (2006.01)

(52) U.S. Cl.
USPC ............................................ 514/289; 546/74

(58) Field of Classification Search
USPC .......................................... 514/289; 546/74
See application file for complete search history.

(56) References Cited

U.S. PATENT DOCUMENTS

| | | | |
|---|---|---|---|
| 4,316,888 A | 2/1982 | Nelson | |
| 4,446,140 A | 5/1984 | Nelson | |
| 4,694,010 A | 9/1987 | Musacchio et al. | |
| 4,898,860 A | 2/1990 | Musacchio et al. | |
| 5,166,207 A | 11/1992 | Smith | |
| 5,304,121 A | 4/1994 | Sahatjian | |
| 5,336,980 A | 8/1994 | Levers | |
| 5,350,756 A | 9/1994 | Smith | |
| 5,366,980 A | 11/1994 | Smith | |
| 5,863,927 A | 1/1999 | Smith et al. | |
| 5,886,026 A | 3/1999 | Hunter et al. | |
| 6,099,562 A | 8/2000 | Ding et al. | |
| 6,197,830 B1 | 3/2001 | Frome | |
| 6,207,164 B1 | 3/2001 | Kreuter et al. | |
| 6,221,335 B1 | 4/2001 | Foster | |
| 6,440,710 B1 | 8/2002 | Keinan et al. | |
| RE38,115 E | 5/2003 | Smith et al. | |
| 6,583,152 B2 | 6/2003 | Sosnowski et al. | |
| 6,603,008 B1 | 8/2003 | Ando et al. | |
| 6,803,031 B2 | 10/2004 | Rabinowitz et al. | |
| 7,014,866 B2 | 3/2006 | Infeld et al. | |
| 7,114,547 B2 | 10/2006 | Sullivan et al. | |
| 7,517,990 B2 | 4/2009 | Ito et al. | |
| 7,973,049 B2 * | 7/2011 | Tung .............................. 514/289 |
| 8,188,110 B2 * | 5/2012 | Tung .............................. 514/289 |
| 2001/0044446 A1 | 11/2001 | Phillips et al. | |
| 2002/0103109 A1 | 8/2002 | Glick et al. | |
| 2004/0087479 A1 | 5/2004 | Sosnowski et al. | |
| 2005/0129783 A1 | 6/2005 | McCleary et al. | |
| 2005/0203125 A1 | 9/2005 | Yakatan et al. | |
| 2005/0256147 A1 | 11/2005 | Kim | |
| 2006/0079502 A1 | 4/2006 | Lang | |
| 2006/0094744 A1 | 5/2006 | Maryanoff et al. | |
| 2007/0082929 A1 | 4/2007 | Gant et al. | |
| 2007/0191411 A1 | 8/2007 | Smith | |
| 2007/0197695 A1 | 8/2007 | Potyen et al. | |
| 2008/0103122 A1 | 5/2008 | Veltri | |
| 2011/0230514 A1 | 9/2011 | Tung | |
| 2011/0257214 A1 | 10/2011 | Graham et al. | |
| 2011/0306627 A1 | 12/2011 | Tung | |

FOREIGN PATENT DOCUMENTS

| | | |
|---|---|---|
| CN | 1220667 | 6/1999 |
| CN | 1968697 | 5/2007 |
| GB | 713146 | 8/1954 |
| JP | 60-089474 A | 5/1985 |
| WO | 95/26325 | 10/1995 |
| WO | 96/09044 | 3/1996 |
| WO | 2005/082911 | 9/2005 |
| WO | 2007/118651 | 10/2007 |
| WO | 2008/097924 | 8/2008 |
| WO | 2008/137474 | 11/2008 |
| WO | 2010/033801 | 3/2010 |

OTHER PUBLICATIONS

Authorized Officer K. Madalinska, International Search Report and Written Opinion of the International Searching Authority, PCT/US2009/062783, mailed Apr. 22, 2010, 26 pages.
Authorized officer Lee W. Young, International Search Report/Written Opinion in PCT/US10/27990 mailed Mar. 19, 2010, 11 pages.
Authorized Officer Nora Lindner, International Preliminary Report on Patentability, PCT/US2009/062783, issued May 3, 2011, 15 pages.
Extended European Search Report in European Application No. 11000764.8, dated May 25, 2011, 8 pages.
Extended European Search Report in European Application No. 11180603.0, dated Jan. 25, 2012, 10 pages.
Extended European Search Report in European Application No. 11188848.3, dated Dec. 23, 2011, 8 pages.

(Continued)

*Primary Examiner* — Charanjit Aulakh
(74) *Attorney, Agent, or Firm* — Fish & Richardson P.C.

(57) ABSTRACT

This disclosure relates to novel morphinan compounds and their derivatives, pharmaceutically acceptable salts, solvates, and hydrates thereof. This disclosure also provides compositions comprising a compound of this disclosure and the use of such compositions in methods of treating diseases and conditions that are beneficially treated by administering a $\sigma_1$ receptor agonist that also has NMDA antagonist activity.

7 Claims, 6 Drawing Sheets

(56) References Cited

OTHER PUBLICATIONS

Extended European Search Report in European Application No. 12176544.0, dated Oct. 12, 2012, 4 pages.
Extended European Search Report in European Application No. 12176476.5, dated Oct. 12, 2012, 4 pages.
International Preliminary Report on Patentability in International Application No. PCT/US2009/062783, mailed May 12, 2011, 15 pages.
International Preliminary Report on Patentability in International Application No. PCT/US2008/062089, mailed Nov. 12, 2009, 8 pages.
International Preliminary Report on Patentability in International Application No. PCT/US2009/057476, mailed Mar. 31, 2011, 9 pages.
International Search Report and Written Opinion in International Application No. PCT/US2009/062783, mailed Apr. 22, 2010, 26 pages.
International Search Report and Written Opinion in International Application No. PCT/US2009/057476, mailed Nov. 12, 2009, 2009, 17 pages.
International Search Report/Written Opinion in International Application No. PCT/US2008/062089, mailed Aug. 12, 2008, 11 pages.
"Dastosin Syrup," *Prospectus*, 2007, 4 pages.
"Dastosin," Patient Information Leaflet, 2002, Ministry of Health Social Politics and Equality (Spanish version and English translation).
"Patient Information: Dextromethorphan," *Medline Plus*, Last Revised Dec. 1, 2008, 6 pages.
"Promethazine HCL and Dextromethorphan Hydrobromide-promethazine hydrochloride and dextromethorphan hydrobromide solution," *ANI Pharmaceuticals, Inc.*, Last Revised May 2008, 6 pages.
"Promethazine Hydrochloride and Dextromethorphan Hydrobromide-promethazine hydrochloride and dextromethorphan hydrobromide syrup," *Actavis Mid Atlantic LLC*, Last Revised Jun. 2006, 6 pages.
Anastasia et al., "Simple and selective one-pot replacement of the N-methyl group of tertiary amines by quaternization and demethylation with sodium sulfide or potassium thioacetate: an application to the synthesis of pergolide." *J. Chem. Soc.*, Perkin Trans.1, 2001, 19:2398-2403.
Baillie, "The use of Stable Isotopes in Pharmacological Research," *Pharmacological Reviews*, 1981, 33(2):81-132.
Barnhart, "The Urinary Excretion of Dextromethorphan and Three Metabolites in Dogs and Humans," *Toxicol. Appl. Pharmacol.*, 1980, 55:43-48.
Belleau et al, "Clastic Binding on the Opiate Receptor," *J. Med Chem.*, 1974, 17(8):908-909.
Blake et al., "Studies with deuterated drugs," *J. Pharm Sci.*, 1975, 64:367-391.
Bölcskei et al., "Synthesis of Deuterated dextromethorphan derivatives," *Arkivok*, 2008, 3:182-193.
Brown et al., "Organoboranes. 39. Convenient procedures for the preparation of methylboronic acid and trimethylboroxin," *Organometallics*, 1985, 4:816-821.
Browne, "Stable Isotope Techniques in Early Drug Development: An Economic Evaluation," *J Clin. Pharmacol.*, 1998, 38:213-220.
Capon et al., "The influence of CYP2D6 polymorphism and quinidine on the disposition and antitussive effect of dextromethorphan in humans," *Clin. Pharmacol. Ther.*, 1996, 60:295-307.
Cherrah et al., "Study of Deuterium Isotope Effects on Protein Binding by Gas chromatography/Mass Spectrometry. Caffeine and Deuterated isotopomers," *Biomed. Environ. Mass. Spect.*, 1987, 14:653-657.
Chou et al., "Dimemorfan N-demethylation by mouse liver microsomal cytochrome P450 enzymes," *Life Sciences*, 2005, 77: 735-745.

Chou et al., "The oxidative metabolism of dimemorfan by human cytochrome P450 enzymes." *J. of Pharma. Sciences*, 2009, pp. 1-15
Dyck et al., "Effects of Deuterium Substitution on the Catabolism of β-Phenylethylamine: An In Vivo Study," *J. Neurochem.*, 1986, 46:399-404.
Eichhold et al., "Highly sensitive high-performance liquid chromatographic-tandem mass spectrometric method for the analysis of dextromethorphan in human plasma," *J. Chromatography B*, 1997, 698:147-154.
Fisher et al., "The complexities inherent in attempts to decrease drug clearance by blocking sites of CYP-mediated metabolism," *Curr Opin Drug Discov Devel.*, 2006, 9:101-109.
Foster, "Deuterium isotope effects in metabolism of drugs and xenobiotics: implications for drug design," *Adv Drug Res.*, 1985, 14:1-40.
Foster, "Deuterium isotope effects in studies of drug metabolism," *Trends in Pharmacological Sciences*, Jan. 1, 1984, 5:524-527.
Freireich et al., "Quantitative comparison of toxicity of anticancer agents in mouse, rat, hamster, dog, monkey, and man," *Cancer Chemother.*, 1966, 50:219-244.
Freshney, "Culture of Animal Cells: A manual of basic technique," John Wiley and Sons, 2005, 5th edition, 7 pages.
Fukuto et al., "Determination of the Mechanism of Demethylenation of (Methy 1 enedioxy)phenyl Compounds by Cytochrome P450 Using Deuterium Isotope Effects," *J. Med. Chem.*, 1991, 34:2871-2876.
Ganapathy et al., "Molecular and ligand-binding characterization of the s-receptor in the Jurkat human T lymphocyte cell line," *J. Pharmacol Exp Ther.*, 1999, 289:251-260.
Gannes et al., "Natural Abundance Variations in Stable Isotopes and their Potential Uses in Animal Physiological Ecology," *Comp Biochem Physiol Mol Integr Physiol.*, 1998, 119:725-737.
Goldman et al., "Differentiation of [.H] phencyclidine and (+)-[.H]SKF-10047 binding sites in rat cerebral cortex," *FEBS Lett.*, 1985, 190:333-336.
Gouyette, "Synthesis of Deuterium-labelled Elliptinium and its Use in Metabolic Studies," *Biomed. Environ. Mass Spect.*, 1988, 15:243-347.
Haskins, "The Application of Stable Isotopes in Biomedical Research," *Biomedical Mass Spectrometry*, 1982, 9(7):269-277.
Heinkele and Muerdter, "Synthesis of [$^2$H]-labelled phase-I-metabolites using 1[$^2$H]-pyridinium hydrochloride," *J. Labelled Compounds Radiopharmaceuticals*, 2005, 48(6):457-461.
Heinkele et al., "Synthesis of [$^2$H$_3$]-dextromethorphan and its major urinary metabolites [$^2$H$_3$]-dextrorphan and [$^2$H$_3$]-dextrorphan-β-glucuronide," *Journal of Labelled Compounds and Radiopharmaceuticals*, 2002, 45(13):1153-1158.
Honma et al., "The metabolism of Roxatidine Acetate Hydrochloride: Liberation of Deuterium from the Piperdine Ring during Hydroxylation," *Drug Metabolism and Disposition*, 1987, 14(4):551-559.
Houston et al., "Prediction of hepatic clearance from microsomes, hepatocytes, and liver slices," *Drug Metab. Rev.*, 1997, 29:891-922.
Houston, "Utility of in vitro drug metabolism data in predicting in vivo metabolic clearance," *Biochem. Pharmacol.*, 1994, 47:1469-1479.
Ida, "The nonnarcotic Antitussive Drug Dimemorfan: A Review," *Clinical Therapeutics*, 1997, 19(2): 215-231.
Iwatsubo et al., "Prediction of in vivo drug metabolism in the human liver from in vitro metabolism data," *Pharmacol. Ther.*, 1997, 73:147-171.
Kerry et al., "The role of CYP2D6 in primary and secondary oxidative metabolism of dextromethorphan: in vitro studies using human liver microsomes," *Br. J. Clin. Pharmacol.*, 1994, 38:243-248.
Kim et al., "Anticonvulsant effects of new morphinan derivatives," *Bioorganic & Medicinal Chemistry Letters*, 2001, 11(13):1651-1654.
Kushner et al., "Pharmacological uses and perspectives of heavy water and deuterated compounds," *Can J Physiol Pharmacol.*, 1999, 77(2):79-88.
Lave et al., "The use of human hepatocytes to select compounds based on their expected hepatic extraction ratios in humans," *Pharm. Res.*, 1997, 14:152-155.

(56) References Cited

OTHER PUBLICATIONS

Magnus, "Nonepileptic uses of gabapentin," *Epilepsia*, 1999, 40:S66-S72.

Miller et al., "Dextromethorphan psychosis, dependence and physical withdrawal," *Addict Biol.*, 2005, 10(4):325-327.

Miller et al., "Therapeutic use of dextromethorphan: Key learnings from treatment of pseudobulbar affect," *J Neurol Sci.*, Aug 15, 2007 259(1-2):67-73, Epub Apr. 16, 2007.

Morganroth et al., "Comparative Study of Encainide and Quinidine in the Treatment of Ventricular Arrhythmias," *JACC*, 1986, 7:9-16.

Nahas et al. "Rapid response of emotional incontinence to selective serotonin reuptake inhibitors." *J. of Neuropsychiatry and Clinical Neuroscience*, 1998, 10(4):453-455.

Newman et al., "Synthesis and evaluation of 3-substituted 17-methylmorphinan analogs as potential anticonvulsant agents," *Journal of Medicinal Chemistry*, 1992, 35(22):4135-4142.

Nicholson et al., "Evaluation of the reinforcing properties and phencyclidine-like discriminative stimulus effects of dextromethorphan and dextrorphan in rats and rhesus monkeys," *Psychopharmacology (Berl)*, 1999, 146(1):49-59.

Obach, "Prediction of human clearance of twenty-nine drugs from hepatic microsomal intrinsic clearance data: An examination of in vitro half-life approach and nonspecific binding to microsomes," *Drug Metab. Disp.*, 1999, 27:1350.

Pender et al., "Toxicity with dextromethorphan-containing preparations: a literature review and report of two additional cases," *Pediatr. Emerg. Care*, 1991, 7:163-167.

Pieniaszek et al., "Moricizine bioavailability via simultaneous, dual, stable isotope administration: bioequivalence implications," *J. Clin. Pharmacol.*, 1999, 39:817-825.

Richter et al., "Synthesis of deuterated dextromethorphan derivatives," ARKIVOC: Free Online Journal of Organic Chemistry, Mar. 1, 2008, 2008(3):182-193.

Sawa et al., "Abnormal osmium tetroxide oxidation of N-meythlmorphinan derivatives," *Tetrahedron*, 1975, 31(8):953-956.

Schiffer et al. "Review of pseudobulbar affect including a novel and potential therapy." *Journal of Neuropsychiatry and Clinical Neuroscience*, 2005, 17(4):447-454.

Schnider and Grussner, " Oxy-morphinane. (3. Mitteilung). Optisch aktive 3-Oxy-morphinane," *Helv. Chim. Acta.*, 1951, 34(7):2211-2217.

*Scientific Tables*, Geigy Pharmaceuticals, Ardsley, N.Y., 1970, p. 537.

Seliger et al. "Fluoxetine improves emotional incontinence." *Brain Injury*, 1992, 6(3):267-270.

Siegel et al., "Binding of the radiolabeled glycine site antagonist [3H]MDS105,519 to homomeric NMDA-NR1a receptors," *Eur. J. Pharmacol.*, 1996, 312(3):357-365.

Takashima et al., "Evaluation of Dextromethorphan Metabolism Using Hepatocytes from CYP2D6 Poor and Extensive Metabolizers," *Drug Metab. Pharmacokinet.*, 2005, 20(3):177-182.

Tan et al. "Emotional incontinence: a dramatic response to paroxetine." *Australian and New Zealand J. of Medicine*, 1996, 26(6):844.

Tonn et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 1993, 22:633-642.

Tortella, et al., "Novel Anticonvulsant Analogs of Dextromethorphan: Improved Efficacy, Potency, Duration and Side-Effect Profile," *J. of Pharma. and Exp. Thera.*, 1994, 268(2): 727-733.

Wada et al., ["Natural abundance of carbon, nitrogen, and hydrogen isotope ratios in biogenic substances: present and future"], *Seikagaku*, 1994, 66(1):15-29.

Watson et al., "Controlled Release oxycodone relieves neuropathic pain: a randomized controlled trial in painful diabetic neuropathy," *Pain*, 2003, 105:71-78.

Werling et al., "A comparison of the binding profiles of dextromethorphan, memantine, fluoxetine and amitriptyline: Treatment of involuntary emotional expression disorder," *Exp. Neurol.*, 2007, 207:248-257.

Wolen, "The Application of Stable Isotopes to Studies of Drug Bioavailability and Bioequivalence," *J Clin Pharmacol.*, 1986, 26:419-424.

Zawertailo et al., "Psychotropic effects of dextromethorphan are altered by the CYP2D6 polymorphism: a pilot study," *J. Clin. Psychopharmacol.*, 1998, 18(4):332-337.

\* cited by examiner 4 mg/kg of each drug P.O.

A 6 mg quinidine, 1 mg compound 101
B 6 mg quinidine, 1 mg dextromethorphan
C 1.5 mg quinidine, 1mg compound 101
D 1.5 mg quinidine, 1 mg dextromethorphan
E 0.5 mg quinidine, 1 mg dextromethorphan
F 0.5 mg quinidine, 1mg compound 101

MORPHINAN COMPOUNDS

CROSS-REFERENCE TO RELATED APPLICATION

This application is a continuation of U.S. application Ser. No. 13/118,935, filed May 31, 2011, which is a continuation of U.S. patent application Ser. No. 12/112,936, filed Apr. 30, 2008, which claims the benefit of priority under 35 U.S.C. §119 to U.S. Provisional Application Ser. Nos. 60/915,130, filed May 1, 2007, 60/916,662, filed May 8, 2007, and 60/976,044, filed Sep. 28, 2007, the entire contents of which are incorporated by reference in their entirety herein.

BACKGROUND

This disclosure relates to novel morphinan compounds and their derivatives, pharmaceutically acceptable salts, solvates, and hydrates thereof. This disclosure also provides compositions comprising a compound of this disclosure and the use of such compositions in methods of treating diseases and conditions that are beneficially treated by administering a $\sigma_1$ receptor agonist that also has NMDA antagonist activity.

Dextromethorphan is currently one of the most widely used antitussives. Also known by the chemical name (+)-3-methoxy-17-methyl-(9α,13α,14α)-morphinan, dextromethorphan is marketed as Zenvia® and Neurodex® in the form of a product comprising dextromethorphan hydrobromide and quinidine sulfate.

In addition to the physiological activity noted above, dextromethorphan also is an agonist of the $\sigma_2$ receptor, an N-methyl-D-aspartate (NDMA) antagonist, and an α3β4 nicotinic receptor antagonist. Dextromethorphan inhibits neurotransmitters, such as glutamate, from activating receptors in the brain. Uptake of dopamine and serotonin are also inhibited.

Dextromethorphan is approved for use in over the counter cough suppressant products. It is currently in Phase I clinical trials for treating subjects with voice spasms, and Phase III clinical studies for treating Rett Syndrome (http://www.clinicaltrials.gov). Dextromethorphan is being studied with other drugs in a Phase II clinical trial characterizing pain processing mechanisms in subjects with irritable bowel syndrome (http://www.clinicaltrials.gov/). Dextromethorphan is also in Phase I clinical trials for treating hyperalgesia in methadone-maintained subjects (http://www.clinicaltrials.gov/).

In addition, a combination of dextromethorphan hydrobromide and quinidine sulfate is currently in Phase III clinical trials for treating diabetic neuropathy pain. (http://www.clinicaltrials.gov). This drug combination is also in Phase III clinical trials for treating Involuntary Emotional Expression Disorder (IEED), also known as pseudobulbar affect, in subjects suffering from Alzheimer's disease, stroke, Parkinson's disease and traumatic brain injury (http://www.clinicaltrials.gov).

Dextromethorphan is metabolized in the liver. Degradation begins with O- and N-demethylation to form primary metabolites dextrorphan and 3-methoxy-morphinan, both of which are further N- and O-demethylated respectively to 3-hydroxy-morphinan. These three metabolites are believed to be therapeutically active. A major metabolic catalyst is the cytochrome P450 enzyme 2D6 (CPY2D6), which is responsible for the O-demethylation reactions of dextromethorphan and 3-methoxymorphinan. The N-demethylation dextromethorphan and dextrorphan are catalyzed by enzymes in the related CPY3A family. Conjugates of dextrorphan and 3-hydroxymorphinan can be detected in human plasma and urine within hours of ingestion.

Dextromethorphan abuse has been linked to its active metabolite, dextrorphan. The PCP-like effects attributed to dextromethorphan are more reliably produced by dextrorphan and thus abuse potential in humans may be attributable to dextromethorphan metabolism to dextrorphan. (Miller, S C et al., Addict Biol, 2005, 10(4): 325-7, Nicholson, K L et al., Psychopharmacology (Berl), 1999 Sep. 1, 146(1): 49-59, Pender, E S et al., Pediatr Emerg Care, 1991, 7: 163-7). One study on the psychotropic effects of dextromethorphan found that extensive metabolizers (EM's) reported a greater abuse potential compared to poor metabolizers (PM's) providing evidence that dextrorphan contributes to dextromethorphan abuse potential (Zawertailo L A, et al., J Clin Psychopharmacol, 1998 Aug. 18(4): 332-7).

A significant fraction of the population has a functional deficiency in the CYP2D6 enzyme. Thus, because the major metabolic pathway for dextromethorphan requires CYP2D6, the decreased activity results in much greater duration of action and greater drug effects in CYP2D6-deficient subjects. In addition to intrinsic functional deficiency, certain medications, such as antidepressants, are potent inhibitors of the CYP2D6 enzyme. With its slower metabolism in some people, dextromethorphan, especially in combination with other medication(s), can lead to serious adverse events.

A longer than recommended duration of a drug in the body may provide continued beneficial effects, but it may also create or prolong undesired side effects. Undesirable side effects at recommended doses of dextromethorphan therapy include nausea, loss of appetite, diarrhea, drowsiness, dizziness, and impotence.

Accordingly, it is desirable to provide a compound that has the beneficial activities of dextromethorphan and may also have other benefits, e.g., reduced adverse side effects, with a decreased metabolic liability, to further extend its pharmacological effective life, enhance subject compliance, and, potentially, to decrease population pharmacokinetic variability and/or decrease its potential for dangerous drug-drug interactions or decrease the likelihood of dextromethorphan abuse due to the formation of metabolites such as dextrorphan.

DETAILED DESCRIPTION

Definitions

Figure 1:
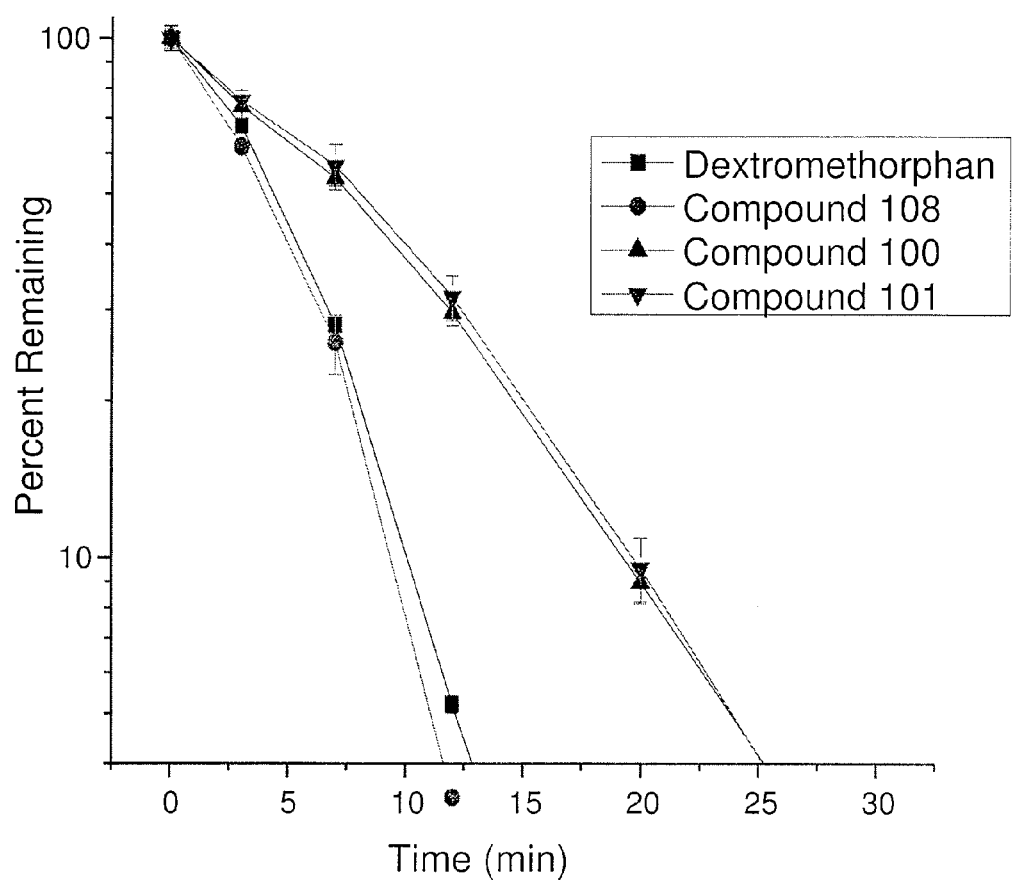
FIG. 1 depicts the stability over time of various compounds of the disclosure in cynomolgus monkey liver microsomes.

The terms "ameliorate" and "treat" are used interchangeably and include therapeutic and/or prophylactic treatment.

Both terms mean decrease, suppress, attenuate, diminish, arrest, or stabilize the development or progression of a disease (e.g., a disease or disorder delineated herein).

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of dextromethorphan will inherently contain small amounts of deuterated and/or $^{13}$C-containing isotopologues. The concentration of naturally abundant stable hydrogen and carbon isotopes, notwithstanding this variation, is small and immaterial as compared to the degree of stable isotopic substitution of compounds of this disclosure. See, for instance, Wada E et al, Seikagaku 1994, 66:15; Ganes L Z et al, Comp Biochem Physiol A Mol Integr Physiol 1998, 119:725. In a compound of this disclosure, when a particular position is designated as having deuterium, it is understood that the abundance of deuterium at that position is substantially greater than the natural abundance of deuterium, which is 0.015%. A position designated as having deuterium typically has a minimum isotopic enrichment factor of at least 3000 (45% deuterium incorporation) at each atom designated as deuterium in said compound.

The term "isotopic enrichment factor" as used herein means the ratio between the isotopic abundance and the natural abundance of a specified isotope.

In other embodiments, a compound of this disclosure has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The term "isotopologue" refers to a species that has the same chemical structure and formula as a specific compound of this disclosure, with the exception of the isotopic composition at one or more positions, e.g., H vs. D. Thus an isotopologue differs from a specific compound of this disclosure in the isotopic composition thereof.

The term "compound," as used herein, is also intended to include any salts, solvates or hydrates thereof.

A salt of a compound of this disclosure is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this disclosure. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

As used herein, the term "hydrate" means a compound which further includes a stoichiometric or non-stoichiometric amount of water bound by non-covalent intermolecular forces.

As used herein, the term "solvate" means a compound which further includes a stoichiometric or non-stoichiometric amount of solvent such as water, acetone, ethanol, methanol, dichloromethane, 2-propanol, or the like, bound by non-covalent intermolecular forces.

The compounds of the present disclosure (e.g., compounds of Formula I), may contain an asymmetric carbon atom, for example, as the result of deuterium substitution or otherwise. As such, compounds of this disclosure can exist as either individual enantiomers, or mixtures of the two enantiomers. Accordingly, a compound of the present disclosure will include both racemic mixtures, and also individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are well known in the art and may be applied as practicable to final compounds or to starting material or intermediates.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"Stereoisomer" refers to both enantiomers and diastereomers.

Throughout this specification, a variable may be referred to generally (e.g., "each R") or may be referred to specifically (e.g., $R^1$ or $R^2$). Unless otherwise indicated, when a variable is referred to generally, it is meant to include all specific embodiments of that particular variable.

Therapeutic Compounds

The present disclosure provides a compound of Formula I, including pharmaceutically acceptable salts, solvates, and hydrates thereof:

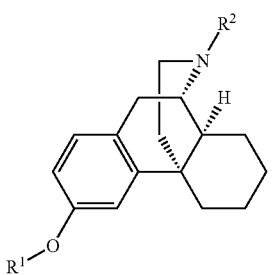

I wherein $R^1$ is selected from $CH_3$, $CH_2D$, $CHD_2$, $CD_3$, $CHF_2$, and $CF_3$; and $R^2$ is selected from $CH_3$, $CH_2D$, $CHD_2$, and $CD_3$.

In certain embodiments, when $R^1$ is $CH_3$, then $R^2$ is not $CH_3$ or $CD_3$. In other embodiments, when $R^1$ is $CD_3$, then $R^2$ is not $CH_3$.

In one embodiment, $R^1$ is selected from $CH_2D$, $CHD_2$, $CD_3$, $CHF_2$, and $CF_3$. In another embodiment, $R^1$ is selected from $CH_2D$, $CHD_2$, and $CD_3$. In a further embodiment, $R^1$ is $CD_3$. In another embodiment, $R^1$ is $CF_3$. In a further embodiment, $R^1$ is $CHF_2$.

In one embodiment, $R^2$ is $CH_3$, $CHD_2$ or $CD_3$. In another embodiment, $R^2$ is $CH_3$. In another embodiment, $R^2$ is $CD_3$.

In yet another embodiment, the compound is selected from any one of the compounds set forth in Table 1.

TABLE 1

Exemplary Compounds of Formula I

| Compound No. | $R^1$ | $R^2$ |
|---|---|---|
| 100 | $CD_3$ | $CH_3$ |
| 101 | $CD_3$ | $CD_3$ |
| 102 | $CD_2H$ | $CD_3$ |
| 103 | $CD_3$ | $CD_2H$ |
| 104 | $CF_3$ | $CH_3$ |
| 105 | $CF_3$ | $CD_3$ |
| 106 | $CHF_2$ | $CH_3$ |
| 107 | $CHF_2$ | $CD_3$ |
| 108 | $CH_3$ | $CD_3$ |

In another set of embodiments, any atom not designated as deuterium in any of the embodiments set forth above is present at its natural isotopic abundance.

In another set of embodiments, the compound of Formula I is isolated or purified, e.g., the compound of Formula I is present at a purity of at least 50% by weight (e.g., at least 55%, 60%, 65%, 70%, 75%, 80%, 85%, 90%, 95%, 97%, 98%, 98.5%, 99%, 99.5% or 99.9%) of the total amount of isotopologues of Formula I present, respectively. Thus, in some embodiments, a composition comprising a compound of Formula I can include a distribution of isotopologues of the compound, provided at least 50% of the isotopologues by weight are the recited compound.

In some embodiments, any position in the compound of Formula I designated as having D has a minimum deuterium incorporation of at least 45% (e.g., at least 52.5%, at least 60%, at least 67.5%, at least 75%, at least 82.5%, at least 90%, at least 95%, at least 97%, at least 99%, or at least 99.5%) at the designated position(s) of the compound of Formula I. Thus, in some embodiments, a composition comprising a compound of Formula I can include a distribution of isotopologues of the compound, provided at least 45% of the isotopologues include a D at the designated position(s).

In some embodiments, a compound of Formula I is "substantially free of" other isotopologues of the compound, e.g., less than 50%, less than 25%, less than 10%, less than 5%, less than 2%, less than 1%, or less than 0.5% of other isotopologues are present.

The synthesis of compounds of Formula I can be readily achieved by synthetic chemists of ordinary skill. Relevant procedures and intermediates are disclosed, for instance in Kim H C et al., Bioorg Med Chem Lett 2001, 11:1651 and Newman A H et al., J Med Chem 1992, 35:4135.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I substitutes the appropriate deuterated intermediates and reagents in synthesis methods utilized for the preparation of dextromethorphan. Compounds of Formula I may be prepared from one of the known intermediates X, XI, and XII shown below, and from related intermediates that may be readily obtained from known procedures.

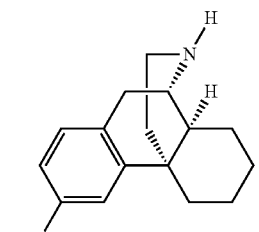

X

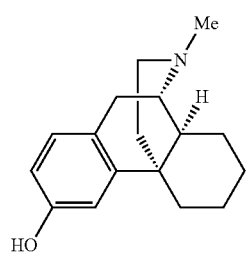

XI

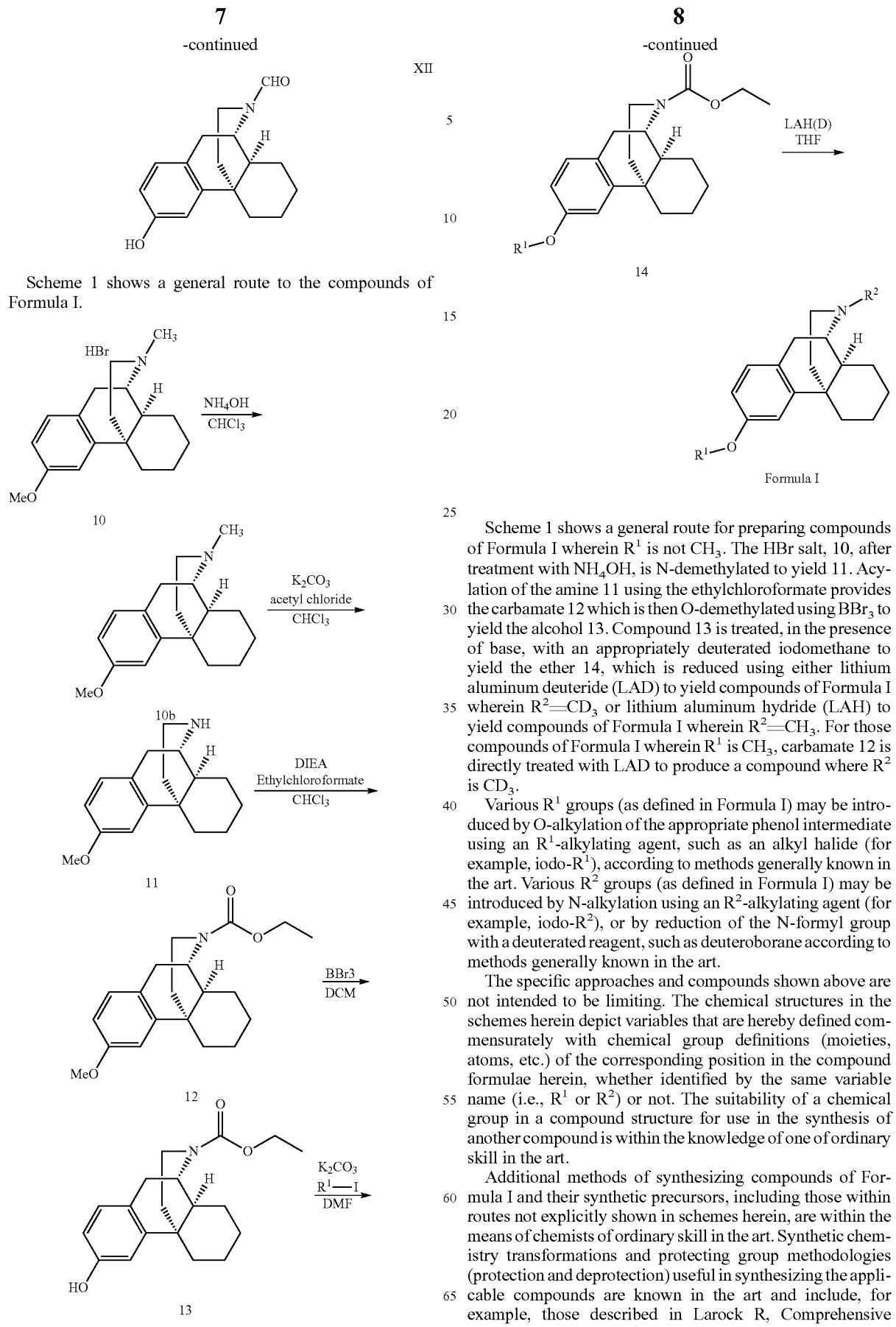

Scheme 1 shows a general route for preparing compounds of Formula I wherein $R^1$ is not $CH_3$. The HBr salt, 10, after treatment with $NH_4OH$, is N-demethylated to yield 11. Acylation of the amine 11 using the ethylchloroformate provides the carbamate 12 which is then O-demethylated using $BBr_3$ to yield the alcohol 13. Compound 13 is treated, in the presence of base, with an appropriately deuterated iodomethane to yield the ether 14, which is reduced using either lithium aluminum deuteride (LAD) to yield compounds of Formula I wherein $R^2$=$CD_3$ or lithium aluminum hydride (LAH) to yield compounds of Formula I wherein $R^2$=$CH_3$. For those compounds of Formula I wherein $R^1$ is $CH_3$, carbamate 12 is directly treated with LAD to produce a compound where $R^2$ is $CD_3$.

Various $R^1$ groups (as defined in Formula I) may be introduced by O-alkylation of the appropriate phenol intermediate using an $R^1$-alkylating agent, such as an alkyl halide (for example, iodo-$R^1$), according to methods generally known in the art. Various $R^2$ groups (as defined in Formula I) may be introduced by N-alkylation using an $R^2$-alkylating agent (for example, iodo-$R^2$), or by reduction of the N-formyl group with a deuterated reagent, such as deuteroborane according to methods generally known in the art.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$ or $R^2$) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, Comprehensive Organic Transformations, VCH Publishers (1989); Greene T W et al., *Protective Groups in Organic Synthesis*, 3rd Ed., John Wiley and Sons (1999); Fieser L et al., Fieser and Fieser's Reagents for Organic Synthesis, John Wiley and Sons (1994); and Paquette L, ed., Encyclopedia of Reagents for Organic Synthesis, John Wiley and Sons (1995) and subsequent editions thereof.

Combinations of substituents and variables envisioned by this disclosure are only those that result in the formation of stable compounds.

Compositions

The disclosure also provides pyrogen-free compositions comprising an effective amount of a compound of Formula I (e.g., including any of the formulae herein), or a pharmaceutically acceptable salt, solvate, or hydrate of said compound; and an acceptable carrier. Preferably, a composition of this disclosure is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present disclosure in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866; and United States patent publications 2006/0094744 and 2006/0079502.

The pharmaceutical compositions of the disclosure include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active.

Where an organ or tissue is accessible because of removal from the subject, such organ or tissue may be bathed in a medium containing a composition of this disclosure, a composition of this disclosure may be painted onto the organ, or a composition of this disclosure may be applied in any other convenient way.

In another embodiment, a composition of this disclosure further comprises a second therapeutic agent. The second therapeutic agent may be selected from any compound or therapeutic agent known to have or that demonstrates advantageous properties when administered with a compound having the same mechanism of action as dextromethorphan. Such agents include those indicated as being useful in combination with dextromethorphan, including but not limited to, those described in U.S. Pat. Nos. 4,316,888; 4,446,140; 4,694,010; 4,898,860; 5,166,207; 5,336,980; 5,350,756; 5,366,980; 5,863,927; RE38,115; 6,197,830; 6,207,164; 6,583,152; and 7,114,547; as well as in US patent publications 2001/0044446; 2002/0103109; 2004/0087479; 2005/0129783; 2005/0203125; and 2007/0191411.

Preferably, the second therapeutic agent is an agent useful in the treatment or prevention of a disease or condition selected from emotional lability; pseudobulbar affect; autism; neurological disorders and neurodegenerative diseases, such as, e.g., dementia, amyotrophic lateral sclerosis (ALS, also known as Leu Gehrig's disease), Alzheimer's disease, Parkinson's disease, and multiple sclerosis; disturbances of consciousness disorders; brain injuries, such as, e.g., stroke, traumatic brain injury, ischemic event, hypoxic event and neuronal death; disturbances of consciousness disorders; cardiovascular diseases, such as, e.g., peripheral vascular diseases, myocardial infarctions, and atherosclerosis; glaucoma, tardive dyskinesia; diabetic neuropathy; retinopathic diseases; diseases or disorders caused by homocysteine-induced apoptosis; diseases or disorders caused by elevated levels of homocysteine; chronic pain; intractable pain; neuropathic pain, sympathetically mediated pain, such as, allodynia, hyperpathia, hyperalgesia, dysesthesia, paresthesia, deafferentation pain, and anesthesia dolorosa pain; pain associated with gastrointestinal dysfunction, including, e.g., irritable bowel syndrome; mouth pain; epileptic seizures; tinnitus; sexual dysfunction; intractable coughing; dermatitis; addiction disorders, such as, e.g., addiction to or dependence on stimulants, nicotine, morphine, heroine, other opiates, amphetamines, cocaine, and alcohol; Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; and fatigue caused by cancer.

In one embodiment, the second therapeutic agent is selected from quinidine, quinidine sulfate, LBH589 (Novartis), oxycodone, and gabapentin.

In another embodiment, the disclosure provides separate dosage forms of a compound of this disclosure and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the disclosure, the compound of the present disclosure is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this disclosure can range from 0.4 mg to 400 mg, from 4.0 mg to 350 mg, from 10 mg to 90 mg, or from 30 mg to 45 mg, inclusive.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for dextromethorphan.

The compounds of the present disclosure and the pharmaceutical compositions that comprise them demonstrate a longer clearance and produce a higher plasma exposure level 12 hours post-dosing as compared to a pharmaceutical composition comprising the same amount of dextromethorphan on a mole basis ("molar equivalent dextromethorphan composition"). Thus, in one embodiment, the disclosure provides a pharmaceutical composition comprising an effective amount of a compound of Formula I, the administration of which to a subject results in a plasma exposure level that is greater than the plasma exposure level of a molar equivalent dextromethorphan composition that is administered using the same dosing regimen.

In another embodiments, the plasma exposure level is at least 110%, 115%, 120% 125%, 130%, 135%, 140%, 145%, or more of the plasma exposure level of dextromethorphan produced by a molar equivalent dextromethorphan composition that is administered to an equivalent subject.

In another embodiment, the disclosure provides a pharmaceutical composition comprising 10-60 mg of a compound of Formula I, wherein the administration of the pharmaceutical composition to a subject results in a plasma exposure level in the range of 250-750 nanograms (ng)-hour (h)/mL (AUC).

In another embodiment, the disclosure provides a pharmaceutical composition comprising 10-60 mg of a compound of Formula I, wherein the administration of the pharmaceutical composition to a subject results in a plasma exposure level in the range of 400-1600 ng-h/mL (AUC).

In another embodiment, the disclosure provides a pharmaceutical composition comprising 10-60 mg of a compound of Formula I, wherein the administration of the pharmaceutical composition to a subject results in a plasma exposure level in the range of 500-1500 ng-h/mL (AUC).

In another embodiment, the disclosure provides a pharmaceutical composition comprising 10-60 mg of a compound of Formula I, wherein the administration of the pharmaceutical composition to a subject results in a plasma exposure level in the range of 1000-1500 ng-h/mL (AUC).

In another embodiment, the disclosure provides a pharmaceutical composition comprising an effective amount of a compound of Formula I, the administration of which to a subject results in a decrease in rate and amount of metabolite production as compared to a molar equivalent dextromethorphan composition that is administered using the same dosing regimen.

In another embodiment, the disclosure provides a pharmaceutical composition comprising 10-60 mg of a compound of Formula I, the administration of which to a subject results in a plasma exposure level of deuterated dextrorphan isotopologues less than or equal to 1000 ng-h/mL.

In another embodiment, the disclosure provides a pharmaceutical composition comprising 10-60 mg of a compound of Formula I, the administration of which to a subject results in a plasma exposure level of deuterated dextrorphan isotopologues less than or equal to 750 ng-h/mL.

In another embodiment, the disclosure provides a pharmaceutical composition comprising 10-60 mg of a compound of Formula I, the administration of which to a subject results in a plasma exposure level of deuterated dextrorphan isotopologues less than or equal to 500 ng-h/mL.

In another embodiment, the disclosure provides a pharmaceutical composition comprising an effective amount of a compound of Formula I, the administration of which to a subject results in both an increase in the plasma exposure level of a compound of Formula I and a decrease in the plasma exposure level of dextromethorphan metabolite isotopologues, particularly deuterated dextrorphan isotopologues, as compared to the plasma exposure levels of dextromethorphan and dextrorphan produced from a molar equivalent dextromethorphan composition that is administered in the same dosing regimen.

In another embodiment, the disclosure provides a pharmaceutical composition comprising 10-60 mg of a compound of Formula I, said composition providing a plasma exposure level of a compound of Formula I of from about 1750 to about 250 ng-h/mL after repeated administration to a subject every 12 hours through steady-state conditions.

For pharmaceutical compositions that comprise a second therapeutic agent, an effective amount of the second therapeutic agent is between about 0.01% to 100% of the dosage normally utilized in a monotherapy regime using just that agent. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which are incorporated herein by reference in their entirety.

It is expected that some of the second therapeutic agents referenced above will act synergistically with the compounds of this disclosure. When this occurs, it will allow the effective dosage of the second therapeutic agent and/or the compound of this disclosure to be reduced from that required in a monotherapy. This has the advantage of minimizing toxic side effects of either the second therapeutic agent of a compound of this disclosure, synergistic improvements in efficacy, improved ease of administration or use and/or reduced overall expense of compound preparation or formulation.

Thus, in one embodiment, the disclosure provides a pharmaceutical composition comprising 10-60 mg of a compound of Formula I and 2.5-30 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In another embodiment, the disclosure provides a pharmaceutical composition comprising 10-60 mg of a compound of Formula I and 2.5-20 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In another embodiment, the disclosure provides a pharmaceutical composition comprising 10-60 mg of a compound of Formula I and 2.5-10 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In another embodiment, the disclosure provides a pharmaceutical composition comprising a 15-45 mg of a compound of Formula I and 2.5-30 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In another embodiment, the disclosure provides a pharmaceutical composition comprising a 20-35 mg of a compound of Formula I and 2.5-30 mg quinidine, said composition providing a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

In another embodiment, the disclosure provides a pharmaceutical composition comprising a compound of Formula I and quinidine, said composition providing lower urine concentrations of a compound of Formula I and higher urine concentrations of deuterated dextrorphan isotopologues in a subject as compared to urine concentrations of dextromethorphan and dextrorphan in an equivalent subject resulting from the administration of a molar equivalent dextromethorphan composition additionally comprising the same amount of quinidine and administered according to the same dosing regimen.

Methods of Treatment

In another embodiment, the disclosure provides a method of modulating the activity of the $\sigma_2$ receptor, N-methyl-D-aspartate (NDMA), or the activity of the $\alpha3\beta4$ nicotinic receptor in a cell, comprising contacting a cell with one or more compounds of Formula I.

In another embodiment, the disclosure provides a method of inhibiting neurotransmitters, such as glutamate, from activating receptors in the brain and/or inhibiting the uptake of dopamine and serotonin by administering a compound of Formula I.

According to another embodiment, the disclosure provides a method of treating a subject suffering from, or susceptible to, a disease that is beneficially treated by dextromethorphan comprising the step of administering to said subject an effective amount of a compound of Formula I wherein $R^1$ is selected from $CH_3$, $CH_2D$, $CHD_2$, $CD_3$, $CHF_2$, and $CF_3$; and $R^2$ is selected from $CH_3$, $CH_2D$, $CHD_2$, and $CD_3$ or a composition comprising such a compound. Such diseases are well known in the art and are disclosed in, but not limited to, those described in U.S. Pat. Nos. 4,316,888; 4,446,140; 4,694,010; 4,898,860; 5,166,207; 5,336,980; 5,350,756; 5,366,980; 5,863,927; RE38,115; 6,197,830; 6,207,164; 6,583,152; and 7,114,547; as well as in US patent publications 2001/0044446; 2002/0103109; 2004/0087479; 2005/0129783; 2005/0203125; and 2007/0191411.

Such diseases include, but are not limited to, emotional lability; pseudobulbar affect; autism; neurological disorders and neurodegenerative diseases, such as, e.g., dementia, amyotrophic lateral sclerosis (ALS, also known as Leu Gehrig's disease), Alzheimer's disease, Parkinson's, and multiple sclerosis; disturbances of consciousness disorders; brain injuries, such as, e.g., stroke, traumatic brain injury, ischemic event, hypoxic event and neuronal death; disturbances of consciousness disorders; cardiovascular diseases, such as, e.g., peripheral vascular diseases, strokes, myocardial infarctions, and atherosclerosis; glaucoma, tardive dyskinesia; diabetic neuropathy; retinopathic diseases; diseases or disorders caused by homocysteine-induced apoptosis; diseases or disorders caused by elevated levels of homocysteine; chronic pain; intractable pain; neuropathic pain, sympathetically mediated pain, such as, allodynia, hyperpathia, hyperalgesia, dysesthesia, paresthesia, deafferentation pain, and anesthesia delorosa pain; pain associated with gastrointestinal dysfunction, including, e.g., irritable bowel syndrome; mouth pain; epileptic seizures; tinnitus; sexual dysfunction; intractable coughing; dermatitis; addiction disorders, such as, e.g., addiction to or dependence on stimulants, nicotine, morphine, heroine, other opiates, amphetamines, cocaine, and alcohol; Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; and fatigue caused by cancer.

In one particular embodiment, the method of this disclosure is used to treat a subject suffering from or susceptible to a disease or condition selected from diabetic neuropathy, Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; and fatigue caused by cancer.

In one particular embodiment, the compound of Formula I, wherein $R^1$ is selected from $CH_3$, $CH_2D$, $CHD_2$, $CD_3$, $CHF_2$, and $CF_3$; and $R^2$ is selected from $CH_3$, $CH_2D$, $CHD_2$, and $CD_3$ or a composition comprising such compound is used to treat a subject suffering from or susceptible neuropathic pain. In another embodiment, the compound is used to treat a subject suffering from pseudobulbar affect.

Methods delineated herein also include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In the methods delineated herein, a pharmaceutical composition comprising an effective amount of a compound of Formula I is adminstered to a subject, resulting in a plasma exposure level that is greater than the plasma exposure level of a molar equivalent dextromethorphan composition that is administered using the same dosing regimen. The plasma exposure level is at least 110%, 115%, 120% 125%, 130%, 135%, 140%, 145%, or more of the plasma exposure level of dextromethorphan produced by a molar equivalent dextromethorphan composition that is administered to an equivalent subject.

In another embodiment, the disclosure provides a method for treating a disease in a subject in need of such treatment, said method comprising administering to the subject a pharmaceutical composition comprising 10-60 mg of a compound of Formula I, wherein the administration of the pharmaceutical composition to the subject results in a plasma exposure level in the range of 250-750 nanograms (ng)-hour (h)/mL (AUC).

In another embodiment, the disclosure provides a method for treating a disease in a subject in need of such treatment, said method comprising administering to the subject a pharmaceutical composition comprising 10-60 mg of a compound of Formula I, wherein the administration of the pharmaceutical composition to the subject results in a plasma exposure level in the range of 400-1600 ng-h/mL (AUC).

In another embodiment, the disclosure provides a method for treating a disease in a subject in need of such treatment, said method comprising administering to the subject a pharmaceutical composition comprising 10-60 mg of a compound of Formula I, wherein the administration of the pharmaceutical composition to the subject results in a plasma exposure level in the range of 500-1500 ng-h/mL (AUC).

In another embodiment, the disclosure provides a method for treating a disease in a subject in need of such treatment, said method comprising administering to the subject a pharmaceutical composition comprising 10-60 mg of a compound of Formula I, wherein the administration of the pharmaceutical composition to the subject results in a plasma exposure level in the range of 1000-1500 ng-h/mL (AUC).

In another embodiment, the disclosure provides a method for treating a disease in a subject in need of such treatment, said method comprising administering to the subject a pharmaceutical composition comprising an amount of a compound of Formula I, effective to decrease in rate and amount of metabolite production as compared to a molar equivalent dextromethorphan composition that is administered using the same dosing regimen.

In another embodiment, the disclosure provides a method for treating a disease in a subject in need of such treatment, said method comprising administering to the subject a pharmaceutical composition comprising 10-60 mg of a compound of Formula I, the administration of which to a subject results in a plasma exposure level of deuterated dextrorphan isotopologues less than or equal to 1000 ng-h/mL.

In another embodiment, the disclosure provides a method for treating a disease in a subject in need of such treatment, said method comprising administering to the subject a pharmaceutical composition comprising 10-60 mg of a compound of Formula I, the administration of which to a subject results in a plasma exposure level of deuterated dextrorphan isotopologues less than or equal to 750 ng-h/mL.

In another embodiment, the disclosure provides a method for treating a disease in a subject in need of such treatment, said method comprising administering to the subject a pharmaceutical composition comprising 10-60 mg of a compound of Formula I, the administration of which to a subject results in a plasma exposure level of deuterated dextrorphan isotopologues less than or equal to 500 ng-h/mL.

In another embodiment, the disclosure provides a method for treating a disease in a subject in need of such treatment, said method comprising administering to the subject a pharmaceutical composition comprising 10-60 mg of a compound of Formula I, the administration of which to a subject results in both an increase in the plasma exposure level of a compound of Formula I and a decrease in the plasma exposure level of dextromethorphan metabolite isotopologues, particularly deuterated dextrorphan isotopologues, as compared to the plasma exposure levels of dextromethorphan and dextrorphan produced from a molar equivalent dextromethorphan composition that is administered in the same dosing regimen.

In another embodiment, the disclosure provides a method for treating a disease in a subject in need of such treatment, said method comprising administering to the subject a pharmaceutical composition comprising 10-60 mg of a compound of Formula I, said composition providing a plasma exposure level of a compound of Formula I of from about 1750 to about 250 ng-h/mL after repeated administration to a subject every 12 hours through steady-state conditions.

In another embodiment, any of the above methods of treatment comprises the further step of co-administering to the subject one or more second therapeutic agents. The choice of second therapeutic agent may be made from any second therapeutic agent known to be useful for co-administration with dextromethorphan. The choice of second therapeutic agent is also dependent upon the particular disease or condition to be treated. Examples of second therapeutic agents that may be employed in the methods of this disclosure are those set forth above for use in combination compositions comprising a compound of this disclosure and a second therapeutic agent.

In particular, the combination therapies of this disclosure include co-administering to a subject in need thereof a compound of Formula I, wherein $R^1$ is selected from $CH_3$, $CH_2D$, $CHD_2$, $CD_3$, $CHF_2$, and $CF_3$; and $R^2$ is selected from $CH_3$, $CH_2D$, $CHD_2$, and $CD_3$ or a composition comprising such compound; and quinidine sulfate wherein the subject is suffering from or susceptible to diabetic neuropathy.

In another embodiment the disclosure provides a method of treating a subject suffering from non-small cell lung cancer or malignant pleural mesothelioma by co-administering to the subject in need thereof a compound of Formula I, wherein $R^1$ is selected from $CH_3$, $CH_2D$, $CHD_2$, $CD_3$, $CHF_2$, and $CF_3$; and $R^2$ is selected from $CH_3$, $CH_2D$, $CHD_2$, and $CD_3$ or a composition comprising such compound; and LBH589.

The term "co-administered" as used herein means that the second therapeutic agent may be administered together with a compound of this disclosure as part of a single dosage form (such as a composition of this disclosure comprising a compound of the disclosure and an second therapeutic agent as described above) or as separate, multiple dosage forms. Alternatively, the additional agent may be administered prior to, consecutively with, or following the administration of a compound of this disclosure. In such combination therapy treatment, both the compounds of this disclosure and the second therapeutic agent(s) are administered by conventional methods. The administration of a composition of this disclosure, comprising both a compound of the disclosure and a second therapeutic agent, to a subject does not preclude the separate administration of that same therapeutic agent, any other second therapeutic agent or any compound of this disclosure to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the disclosure, where a second therapeutic agent is administered to a subject, the effective amount of the compound of this disclosure is less than its effective amount would be where the second therapeutic agent is not administered. In another embodiment, the effective amount of the second therapeutic agent is less than its effective amount would be where the compound of this disclosure is not administered. In this way, undesired side effects associated with high doses of either agent may be minimized. Other potential advantages (including without limitation improved dosing regimens and/or reduced drug cost) will be apparent to those of skill in the art.

In yet another aspect, the disclosure provides the use of a compound of Formula I alone or together with one or more of the above-described second therapeutic agents in the manufacture of a medicament, either as a single composition or as separate dosage forms, for treatment or prevention in a subject of a disease, disorder or symptom set forth above. Another aspect of the disclosure is a compound of Formula I for use in the treatment or prevention in a subject of a disease, disorder or symptom thereof delineated herein.

Thus, in another embodiment, the disclosure provides a method of treating a disease in a subject in need of such treatment, the method comprising co-administering 10-60 mg of a compound of Formula I and 2.5-30 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in another embodiment, the disclosure provides a method of treating a disease in a subject in need of such treatment, the method comprising co-administering 10-60 mg of a compound of Formula I and 2.5-20 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in another embodiment, the disclosure provides a method of treating a disease in a subject in need of such treatment, the method comprising co-administering 10-60 mg of a compound of Formula I and 2.5-10 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in another embodiment, the disclosure provides a method of treating a disease in a subject in need of such treatment, the method comprising co-administering 15-45 mg of a compound of Formula I and 2.5-30 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in another embodiment, the disclosure provides a method of treating a disease in a subject in need of such treatment, the method comprising co-administering 20-35 mg of a compound of Formula I and 2.5-30 mg quinidine, so that the composition provides a maximum plasma exposure level after repeated administration every 12 to 24 hours through steady-state conditions of a compound of Formula I in a subject of from about 1750 to about 250 ng-h/mL, wherein the administration of said composition to a subject results in a reduction in the plasma exposure level of deuterated dextrorphan isotopologues as compared to the same molar amount of a compound of Formula I administered without the quinidine.

Thus, in another embodiment, the disclosure provides a method of treating a disease in a subject in need of such treatment, the method comprising co-administering a compound of Formula I and quinidine, so that the composition provides lower urine concentrations of a compound of Formula I and higher urine concentrations of deuterated dextrorphan isotopologues in a subject as compared to urine concentrations of dextromethorphan and dextrorphan in an equivalent subject resulting from the administration of a molar equivalent dextromethorphan composition additionally comprising the same amount of quinidine and administered according to the same dosing regimen.

Diagnostic Methods and Kits

The compounds and compositions of this disclosure are also useful as reagents in methods for determining the concentration of dextromethorphan in solution or biological sample such as plasma, examining the metabolism of dextromethorphan and other analytical studies.

According to one embodiment, the disclosure provides a method of determining the concentration, in a solution or a biological sample, of dextromethorphan, comprising the steps of:

a) adding a known concentration of a compound of Formula I to the solution of biological sample;

b) subjecting the solution or biological sample to a measuring device that distinguishes dextromethorphan from a compound of Formula I;

c) calibrating the measuring device to correlate the detected quantity of the compound of Formula I with the known concentration of the compound of Formula I added to the biological sample or solution; and d) measuring the quantity of dextromethorphan in the biological sample with said calibrated measuring device; and e) determining the concentration of dextromethorphan in the solution of sample using the correlation between detected quantity and concentration obtained for a compound of Formula I.

Measuring devices that can distinguish dextromethorphan from the corresponding compound of Formula I include any measuring device that can distinguish between two compounds that differ from one another only in isotopic abundance. Exemplary measuring devices include a mass spectrometer, NMR spectrometer, or IR spectrometer.

In another embodiment, a method for determining the amount of dextromethorphan in a solution or a biological sample is provided, comprising:

a) adding a known amount of a compound of Formula I to the solution or biological sample;

b) detecting at least one signal for a compound of Formula I and at least one signal for dextromethorphan in a measuring device that is capable of distinguishing the two compounds;

c) correlating the at least one signal detected for a compound of Formula I with the known amount of the compound of Formula I added to the solution or the biological sample; and d) determining the amount of dextromethorphan in the solution or biological sample using the correlation between the at least one signal detected of the compound of Formula I and the amount added to the solution or biological sample of a compound of Formula I.

In another embodiment, the disclosure provides a method of evaluating the metabolic stability of a compound of Formula I comprising the steps of contacting the compound of Formula I with a metabolizing enzyme source for a period of time and comparing the amount of the compound of Formula I with the metabolic products of the compound of Formula I after the period of time.

In a related embodiment, the disclosure provides a method of evaluating the metabolic stability of a compound of Formula I in a subject following administration of the compound of Formula I. This method comprises the steps of obtaining a serum, blood, tissue, urine or feces sample from the subject at a period of time following the administration of the compound of Formula I to the subject; and comparing the amount of the compound of Formula I with the metabolic products of the compound of Formula I in the serum, blood, tissue, urine or feces sample.

The present disclosure also provides kits for use to treat diabetic neuropathy, Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; and fatigue caused by cancer. These kits comprise (a) a pharmaceutical composition comprising a compound of Formula I or a salt, hydrate, or solvate thereof, wherein said pharmaceutical composition is in a container; and (b) instructions describing a method of using the pharmaceutical composition to treat pseudobulbar affect; diabetic neuropathy; Rett syndrome (RTT); voice disorders due to uncontrolled laryngeal muscle spasms, including e.g., abductor spasmodic dysphonia, adductor spasmodic dysphonia, muscular tension dysphonia, and vocal tremor; methotrexate neurotoxicity; and fatigue caused by cancer.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In on embodiment, the container is a blister pack.

The kits of this disclosure may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this disclosure may comprise in a separate vessel of container a pharmaceutical composition comprising a second therapeutic agent, such as one of those listed above for use for co-administration with a compound of this disclosure.

EXAMPLES

Example 1

Syntheses of Compounds 100, 101, and 108

Each of the steps and numbered intermediates described below refer to the corresponding steps and intermediates in Scheme 1, supra.

(+)-3-methoxy-17-methyl-(9α,13α,14α)-morphinan (10b)

To a reaction vessel was added (+)-3-methoxy-17-methyl-(9α,13α,14α)-morphinan, HBr salt (3.00 g, 8.5 mmol), NH$_3$ in CH$_3$OH (2.0 M, 8.5 mL, 17.0 mmol), and a stir bar. The reaction mixture was stirred at RT for 1 h. The resulting material was concentrated on a rotary evaporator, then diluted with CHCl$_3$ (50 mL) and H$_2$O (50 mL). The layers were separated and the water layer was extracted with CHCl$_3$ (50 mL). The combined organic layers were dried over magnesium sulfate, filtered and concentrated on a rotary evaporator to yield 2.88 g of 10b as a fluffy white solid.

$^1$H-NMR (300 MHz, CDCl$_3$): δ 1.12 (ddd, J$_1$=24.7, J$_2$=12.6, J$_3$=3.8, 1H), 1.23-1.43 (m, 5H), 1.49-1.52 (m, 1H), 1.62-1.65 (m, 1H), 1.72 (td, $J_1$=12.6, $J_2$=4.9, 1H), 1.81 (dt, $J_1$=12.6, $J_2$=3.3, 1H), 2.07 (td, $J_1$=12.6, $J_2$=3.3, 1H), 2.33-2.47 (m, 5H), 2.57 (dd, $J_1$=18.1, $J_2$=5.5, 1H), 2.79 (dd, $J_1$=5.5, $J_2$=3.3, 1H), 2.98 (d, J=18.1, 1H), 6.68 (dd, $J_1$=8.2, $J_2$=2.7, 1H), 6.80 (d, J=2.7, 1H), 7.02 (d, J=8.8, 1H).

(+)-3-methoxy-(9α,13α,14α)-morphinan (11)

The solid 10b (6.79 g, 25.1 mmol) was placed in a reaction vessel with $CHCl_3$ and a stir bar. $K_2CO_3$ (13.85 g, 100.2 mmol) was added and the mixture was stirred at RT under an atmosphere of $N_2$ for 10 min before the addition of acetyl chloride (7.866 g, 100.2 mmol). The resulting reaction mixture, still under an atmosphere of $N_2$, was stirred under reflux conditions for 7 h, then filtered through a pad of celite. The organic filtrate was concentrated on a rotary evaporator and the resulting crude material was dissolved in $CH_3OH$ then stirred under reflux conditions for 1 h. The solution was concentrated on a rotary evaporator then dried under vacuum to yield 6.78 g of 11 as an off-white solid.

$^1$H-NMR (300 MHz, $CDCl_3$): δ 1.04-1.13 (m, 1H), 1.19-1.29 (m, 1H), 1.37-1.66 (m, 6H), 2.37 (d, J=13.5, 2H), 2.54 (bs, 1H), 2.80 (s, 2H), 2.95-2.99 (m, 1H), 3.12-3.18 (m, 2H), 3.48 (s, 1H), 3.71 (s, 3H), 6.76 (dd, $J_1$=8.3, $J_2$=2.6, 1H), 6.80 (d, J=2.3, 1H), 7.07 (d, J=8.3, 1H).

(+)-17-ethylcarbamate-3-methoxy-(9α,13α,14α)-morphinan (12)

To a reaction vessel fit with a stirbar was added 11 (6.025 g, 2.48 mmol) dissolved in $CHCl_3$ (100 mL). Diisopropylethylamine (DIEA; 16.32 g, 126.3 mmol) was added and the mixture was stirred for 10 min at room temperature under nitrogen before the addition of ethylchloroformate (13.094 g, 76.8 mmol). The reaction mixture was stirred under reflux conditions under nitrogen for 3 h, at which point tlc (20% ethylacetate/hexane) showed complete consumption of starting material, 11. The organic layer was removed and washed first with 1M HCl, and then with saturated $NaHCO_3$. The aqueous layers from each wash were combined and back extracted with 50 mL of $CHCl_3$. The organic layer from the back extraction was combined with the organic layer from the washes and the combined organic layers were dried over $NaSO_4$. The organic solution was then filtered, concentrated on a rotary evaporator then purified via automated flash column chromatography (0-30% ethylacetate/hexane) to yield 5.37 g of 12 as a clear light yellow oil.

$^1$H-NMR (300 MHz, $CDCl_3$): δ 1.06 (ddd, $J_1$=25.3, $J_2$=12.6, $J_3$=3.8, 1H), 1.21-1.39 (m, 7H), 1.45-1.60 (m, 3H), 1.65-1.70 (m, 2H), 2.34-2.37 (m, 1H), 2.54-2.69 (m, 2H), 3.04-3.12 (m, 1H), 3.78 (s, 3H), 3.86 (ddd, $J_1$=42.3, $J_2$=13.7, $J_3$=3.8, 1H), 4.12 (q, J=7.14, 2H), 4.31 (dt, $J_1$=56.6, $J_2$=4.3, 1H), 6.71 (dd, $J_1$=8.8, $J_2$=2.2, 1H), 6.82 (d, J=2.7, 1H), 7.00 (apparent t, J=8.2, 1H).

(+)-17-ethylcarbamate-3-hydroxy-(9α,13α,14α)-morphinan (13)

In a reaction vessel fit with a stirbar the carbamate 12 (2.43 g, 7.4 mmol) was dissolved in DCM (20 mL) and the resulting solution was cooled to 0° C. $BBr_3$ (9.24 g, 36.9 mmol) was added and the reaction mixture was stirred under an atmosphere of $N_2$ at 0° C. for 20 min (at which time tlc in 20% ethylacetate/hexane showed the reaction to be complete). A solution of 27% $NH_4OH$ in ice was placed in a beaker with a stir bar and the reaction mixture was slowly added with stirring. The resulting mixture was stirred for 20 min then was extracted with 4:1 $CHCl_3$/$CH_3OH$ (200 mL). The organic layer was dried over $Na_2SO_4$, filtered, then concentrated on a rotary evaporator. The crude material was purified via automated flash column chromatography ($CH_3OH$ with 1% $NH_4OH$/$CHCl_3$, 0-10%). The pure fractions were concentrated on a rotary evaporator to yield 1.48 g of 13 as a white solid.

$^1$H-NMR (300 MHz, $CDCl_3$): δ 1.04-1.12 (m, 1H), 1.22-1.36 (m, 7H), 1.45-1.59 (m, 3H), 1.63-1.67 (m, 2H), 2.30-2.33 (m, 1H), 2.52-2.66 (m, 2H), 3.06 (dt, $J_1$=18.4, $J_2$=5.9, 1H), 3.84 (ddd, $J_1$=35.8, $J_2$=13.8, $J_3$=6.1, 1H), 4.10-4.18 (m, 2H), 4.31 (dt, $J_1$=53.9, $J_2$=3.1, 1H), 6.64 (m, 1H), 6.78 (s, 1H), 6.93 (apparent t, J=7.8, 1H).

(+)-17-ethylcarbamate-3-$d_3$-methoxy-(9α,13α,14α)-morphinan (14; $R^1$=$CD_3$)

The product 13 (1.48 g, 4.7 mmol) was dissolved in DMF (20 mL) in a reaction vessel fit with a stir bar. To this solution was added $K_2CO_3$ (2.97 g, 21.5 mmol). The mixture was stirred under an atmosphere of $N_2$ at RT for 10 min before the addition of $CD_3I$ (1.02 g, 7.0 mmol). The resulting reaction mixture was stirred overnight at RT at which time tlc (20% ethylacetate/hexane) showed complete reaction. The mixture was diluted with $H_2O$ then was extracted with ethyl ether (3×30 mL). The combined organic layers were dried over $Na_2SO_4$, filtered, and the filtrate concentrated on a rotary evaporator to a clear yellow oil. Purification via automated flash column chromatography (0-20% ethylacetate/hexane) and concentration of pure fractions on a rotary evaporator afforded 793 mg of product.

$^1$H-NMR (300 MHz, $CDCl_3$): δ 1.01-1.11 (m, 1H), 1.22-1.39 (m, 7H), 1.45-1.59 (m, 3H), 1.62-1.70 (m, 2H), 2.34-2.37 (m, 1H), 2.54-2.69 (m, 2H), 3.04-3.12 (m, 1H), 3.84 (ddd, $J_1$=43.2, $J_2$=13.8, $J_3$=4.8, 1H), 4.09-4.17 (m, 2H), 4.31 (dt, $J_1$=56.4, $J_2$=3.4, 1H), 6.71 (dd, $J_1$=8.4, $J_2$=2.5, 1H), 6.82 (d, J=2.7, 1H), 7.00 (apparent t, J=8.2, 1H).

(+)-3-$d_3$-methoxy-17-$d_3$-methyl-(9α,13α,14α)-morphinan (Compound 101)

To a reaction vessel fit with a stir bar, was added THF (5 mL) and LAD (100 mg, 2.4 mmol). The slurry was cooled to 0° C. followed by the addition of a solution of product 14 ($R^1$=$CD_3$, 397 mg, 1.2 mmol) in THF (5 mL). The reaction mixture was stirred under an atmosphere of $N_2$ for 2 h at which time tlc (20% ethylacetate/hexane) showed the reaction to be complete. The mixture was then quenched by the addition of magnesium sulfate heptahydrate until cessation of gas evolution. Ethyl ether (25 mL) was added to the flask, the slurry was filtered, and the organic filtrate was concentrated on a rotary evaporator to an oil. The crude product was purified via automated flash column chromatography ($CH_3OH$ with 1% $NH_4OH$/$CHCl_3$, 0-10%), concentrated on a rotary evaporator, then dissolved in a saturated solution of HBr in dioxane. The mixture was stirred for 10 min, was concentrated on a rotary evaporator, then dried under vacuum for 3 d to yield 204 mg of Compound 101.

$^1$H-NMR (300 MHz, $CDCl_3$): δ 1.08 (ddd, $J_1$=25.1, $J_2$=12.6, $J_3$=3.3, 1H), 1.22-1.32 (m, 1H), 1.35-1.48 (m, 4H), 1.60 (dd, $J_1$=39.0, $J_2$=12.6, 2H), 2.02 (dt, $J_1$=13.2, $J_2$=4.0, 1H), 2.17 (d, J=11.9, 1H), 2.34 (t, J=13.5, 2H), 2.75-2.80 (m, 1H), 2.88 (dd, $J_1$=18.8, $J_2$=5.3, 1H), 3.01 (d, J=18.5, 1H), 3.15 (s, 1H), 6.73 (d, J=8.6, 1H), 6.81 (s, 1H), 7.05 (d, J=8.6, 1H). HPLC (method: 150 mm C18-RP column—gradient method 5-95% ACN; Wavelength: 254 nm): retention time: 6.74 min. MS (M+H$^+$): 278.4.

(+)-3-d$_3$-methoxy-17-methyl-(9α,13α,14α)-morphinan (Compound 100)

To a reaction vessel fit with a stir bar, was added THF (5 mL) and LAH (91 mg, 2.4 mmol). The slurry was cooled to 0° C. followed by the addition of product 14 (R$^1$=CD$_3$, 397 mg, 1.2 mmol) dissolved in THF (5 mL). The reaction mixture was stirred under an atmosphere of N$_2$ for 2 h at which time tlc (20% ethylacetate/hexane) showed the reaction to be complete. The mixture was then quenched by the addition of magnesium sulfate heptahydrate until cessation of gas evolution. Ethyl ether (25 mL) was added to the flask, the slurry was filtered, and the organic filtrate was concentrated on a rotary evaporator to an oil. The crude product was purified via automated flash column chromatography (CH$_3$OH with 1% NH$_4$OH/CHCl$_3$, 0-10%), concentrated on a rotary evaporator, then dissolved in a saturated solution of HBr in dioxane. The mixture was stirred for 10 min, was concentrated on a rotary evaporator, then dried under vacuum for 3 d to yield 200 mg of Compound 100.

$^1$H-NMR (300 MHz, CDCl$_3$): δ 1.07-1.16 (m, 1H), 1.22-1.32 (m, 1H), 1.34-1.46 (m, 4H), 1.59 (dd, J$_1$=41.0, J$_2$=12.6, 2H), 1.94 (t, J=12.6, 1H), 2.06 (d, J=12.9, 1H), 2.26 (t, J=12.6, 1H), 2.36 (d, J=13.2, 1H), 2.53 (s, 3H), 2.67 (d, J=12.2, 1H), 2.78 (dd, J$_1$=18.8, J$_2$=5.0, 1H), 3.06 (d, J=19.2, 2H), 6.72 (d, J=8.3, 1H), 6.81 (s, 1H), 7.05 (d, J=8.6, 1H). HPLC (method: 150 mm C18-RP column—gradient method 5-95% ACN; Wavelength: 254 nm): retention time: 6.86 min. MS (M+H$^+$): 275.2.

(+)-3-methoxy-17-d$_3$-methyl-(9α,13α,14α)-morphinan (Compound 108)

To a reaction vessel fit with a stir bar, was added THF (2 mL) and LAD (99 mg, 2.4 mmol). The slurry was cooled to 0° C. followed by the gradual addition of carbamate 12 (195 mg, 6.0 mmol) dissolved in THF (3 mL). The reaction mixture was stirred under an atmosphere of N$_2$ for 10 min at which time tlc (20% ethylacetate/hexane) showed the reaction to be complete. The mixture was then quenched by the addition of magnesium sulfate heptahydrate until cessation of gas evolution. The resulting solid was washed with ethyl ether, filtered, and the organic filtrate was concentrated on a rotary evaporator to an oil. The crude product was purified via automated flash column chromatography (CH$_3$OH with 1% NH$_4$OH/CHCl$_3$, 90%), concentrated on a rotary evaporator, and then dissolved in a saturated solution of HBr in dioxane. The mixture was stirred for 10 min, and then concentrated on a rotary evaporator to yield 74 mg of product.

$^1$H-NMR (300 MHz, CDCl$_3$): δ 0.96 (ddd, J$_1$=25.4, J$_2$=12.7, J$_3$=3.9, 1H), 1.08-1.18 (m, 1H), 1.24-1.36 (m, 2H), 1.43-1.52 (m, 3H), 1.62 (d, J=12.7, 1H), 1.78 (td, J$_1$=13.7, J$_2$=4.4, 1H), 1.96 (d, J=12.2, 1H), 2.41-2.47 (m, 2H), 2.97 (dd, J$_1$=19.5, J$_2$=5.9, 1H), 3.10-3.18 (m, 2H), 3.60-3.63 (m, 1H), 3.73 (s, 3H), 6.81-6.84 (m, 2H), 7.13 (d, J=9.3, 1H), 9.60 (bs, 1H). HPLC (method: 150 mm C18-RP column—gradient method 5-95% ACN; Wavelength: 280 nm): retention time: 6.91 min. MS (M+H$^+$): 275.7.

Example 2

Microsomal Assays

Certain in vitro liver metabolism studies have been described previously in the following references, each of which is incorporated herein in their entirety: Obach, R S Drug Metab Disp 1999, 27:1350; Houston, J B et al, Drug Metab Rev 1997, 29:891; Houston, J B Biochem Pharmacol 1994, 47:1469; Iwatsubo, T et al, Pharmacol Ther 1997, 73:147; and Lave, T et al, Pharm Res 1997, 14:152.

The objectives of this study were to determine the metabolic stability of the test compounds in pooled human and chimpanzee liver microsomal incubations. Samples of the test compounds, exposed to pooled human or chimp liver microsomes, were analyzed using HPLC-MS (or MS/MS) detection. For determining metabolic stability, multiple reaction monitoring (MRM) was used to measure the disappearance of the test compounds.

Experimental Procedures

Human liver and Cynomolgus monkey liver microsomes were obtained from XenoTech, LLC (Lenexa, Kans.). The incubation mixtures were prepared as follows:

Reaction Mixture Composition

| | |
|---|---|
| Liver Microsomes | 0.5, 1.0 or 2.0 mg/mL |
| NADPH | 1 mM |
| Potassium Phosphate, pH 7.4 | 100 mM |
| Magnesium Chloride | 10 mM |
| Test Compound (Dextromethorphan, Compound 100, Compound 101, Compound 108) | 0.10, 0.25, 1 µM |

Incubation of Test Compounds with Liver Microsomes:

The reaction mixture, minus cofactors, was prepared. An aliquot of the reaction mixture (without cofactors) was incubated in a shaking water bath at 37° C. for 3 minutes. Another aliquot of the reaction mixture was prepared as the negative control. The test compound was added into both the reaction mixture and the negative control at a final concentration of 0.10, 0.25, or 1 µM. An aliquot of the reaction mixture was prepared as a blank control, by the addition of plain organic solvent (no test compound is added). The reaction was initiated by the addition of cofactors (not added to the negative controls), and then incubated in a shaking water bath at 37° C. Aliquots (200 µL) were withdrawn in triplicate at multiple time points and combined with 800 µL of ice-cold 50/50 acetonitrile/dH$_2$O to terminate the reaction. The positive controls, testosterone and propranolol, as well as dextromethorphan, were each run simultaneously with the test compounds in separate reactions.

All samples were analyzed using LC-MS (or MS/MS). An LC-MRM-MS/MS method is used for metabolic stability. For testing in cynomolgus monkey liver microsomes, a final concentration of 1 µM of each compound and 0.5 mg/mL of microsomes were used. FIG. 1 demonstrates that Compound 100 and Compound 101 had greater stability than dextromethorphan in monkey liver microsomes. The stability of Compound 108 in monkey liver microsomes was similar to that of dextromethorphan.

Figure 2:
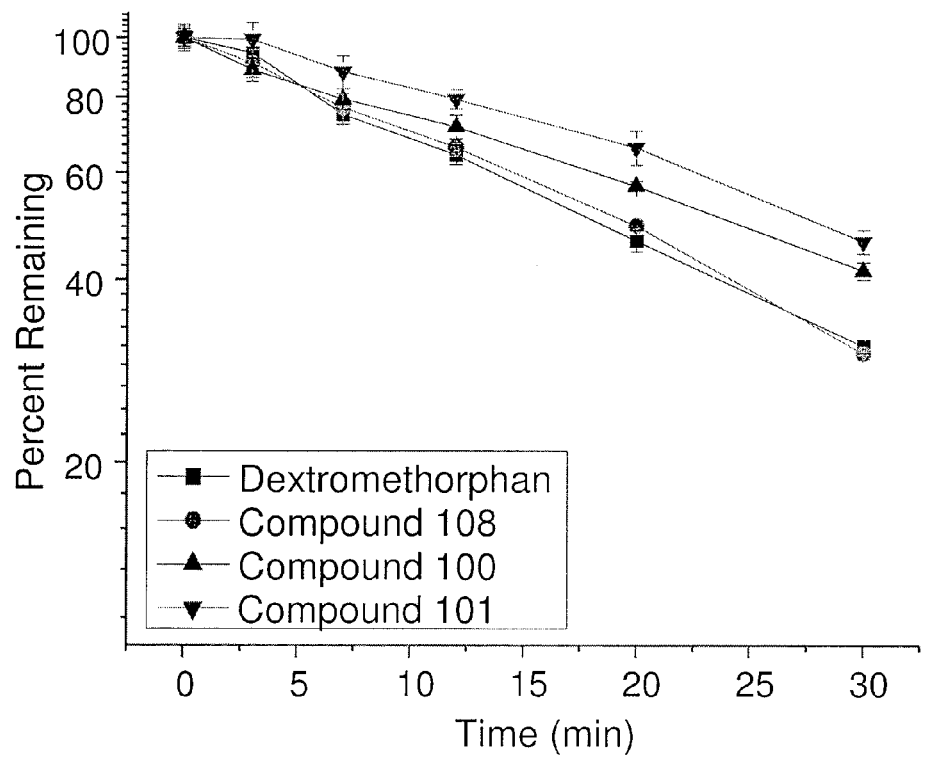
FIG. 2 depicts the stability over time of various compounds of the disclosure in human liver microsomes.

Similar results were obtained using human liver microsomes. FIG. 2 demonstrates that approximately 45% of Compound 101 and 42% of Compound 100 remained intact after 30 minutes of incubation or 0.25 µM of each compound with 2 mg/mL human liver microsomes. In contrast, only about 33% of dextromethorphan was still intact after the same period of time. Compound 108 demonstrated similar stability to dextromethorphan.

The relative stability of Compounds 100 and 101 as compared to dextromethorphan in human liver microsomes remained the same even at a low (0.1 µM) concentration of compound (data not shown). Decreasing the concentration of human liver microsomes slows down the metabolism of all test compounds. After a 30 minute exposure to 0.5 mg/mL approximately 75% of Compound 101 and 71% of Compound 100 remained intact. Dextromethorphan showed a higher lability with only about 65% remaining after the 30 minute incubation.

Example 3

Evaluation of Metabolic Stability in CYP2D6 SUPERSOMES™

Human CYP2D6+P450 Reductase SUPERSOMES™ were purchased from GenTest (Woburn, Mass., USA). A 1.0 mL reaction mixture containing 25 pmole of SUPERSOMES™, 2.0 mM NADPH, 3.0 mM MgCl, and 0.1 µM of various compounds of Formula I (Compounds 100, 101, and 108) in 100 mM potassium phosphate buffer (pH 7.4) was incubated at 37° C. in triplicate. Positive controls contained 0.1 µM dextromethorphan instead of a compound of Formula I. Negative controls used Control Insect Cell Cytosol (insect cell microsomes that lacked any human metabolic enzyme) purchased from GenTest (Woburn, Mass., USA). Aliquots (50 µL) were removed from each sample and placed in wells of a multi-well plate at 0, 2, 5, 7, 12, 20, and 30 minutes and to each was added 50 µL of ice cold acetonitrile with 3 µM haloperidol as an internal standard to stop the reaction.

Plates containing the removed aliquots were then placed in −20° C. freezer for 15 minutes to cool. After cooling, 100 µL of deionized water was added to all wells in the plate. Plates were then spun in the centrifuge for 10 minutes at 3000 rpm. A portion of the supernatant (100 µL) was then removed, placed in a new plate and analyzed using Mass Spectrometry.

Figure 3:
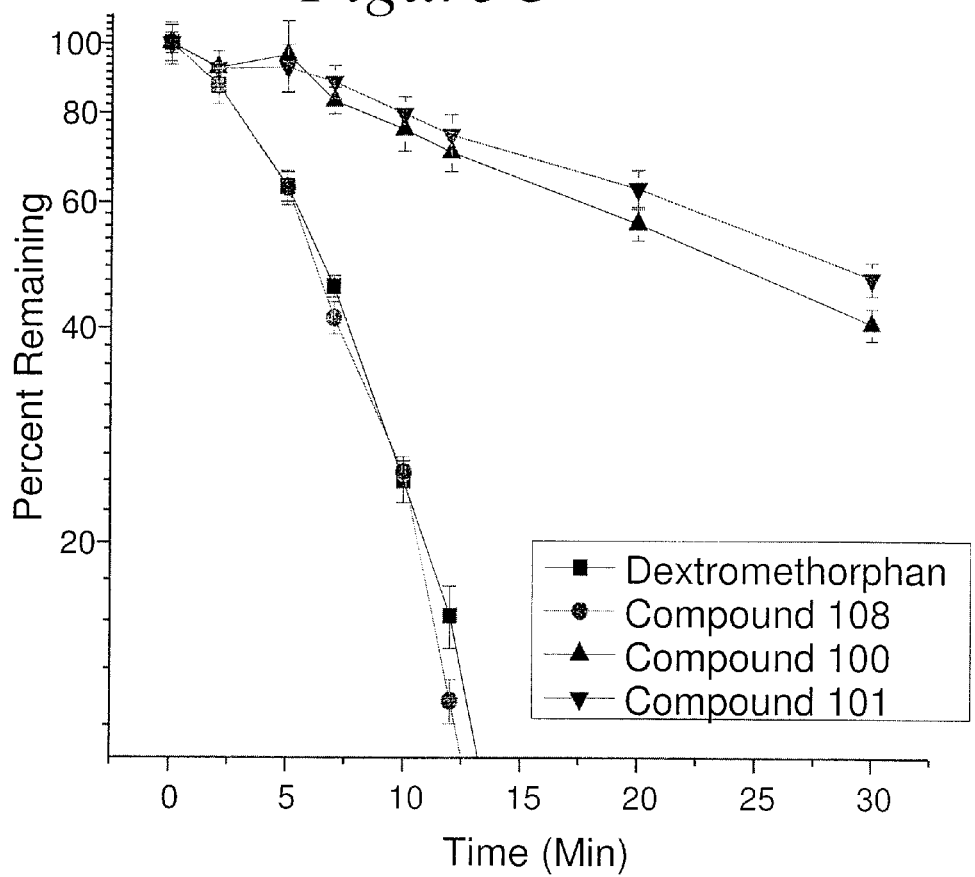
FIG. 3 depicts the stability over time of various compounds of the disclosure in 2D6 Supersomes™.

FIG. 3 shows the results of the Supersomes experiment. Once again Compounds 100 and 101 were much more stable to metabolism than dextromethorphan or Compound 108. Approximately 47% of Compound 101 and 40% of Compound 100 remained intact after a 30 minute incubation with the 2D6 Supersomes™. In contrast, no intact dextromethorphan could be detected at the 20 minute time point.

The above results all suggest that the presence of deuterium at the $R^1$ position in the compounds of this disclosure imparts greater metabolic stability to the compound as compared to dextromethorphan.

Example 4

Evaluation of Pharmacokinetics of Test Articles C20148, and C10003 in Cynomolgus Monkeys Following Oral Administration in Combination with Quinidine OBJECTIVE—The objective of this study was to collect plasma samples from Cynomolgus Monkeys at various time points following oral administration of test articles in combination. The samples were used for the determination of plasma drug levels by LC/MS/MS for estimating pharmacokinetic parameters. This study was conducted in accordance with Shanghai Medicilon Inc. Standard Operating Procedures (SOPs). The Sponsor provided the test compounds and internal standard compound.

Animal Husbandry—The animals used were cynomolgus monkeys, who at the age of initiation of treatment, were 3-4 years of age, and weighed between 4-6 kg.

Environment and Acclimation—Environmental controls for the animal room were set to maintain a temperature of 23±2° C., humidity of 50-70%, and a 12-hour light/12-hour dark cycle. As needed, the 12-hour dark cycle was temporarily interrupted to accommodate study procedures. Animals were previously acclimated to study procedures prior to initial dose administration.

Food and Water—SL-Ml (Shanghai Shilin Biotech Incorporation) were provided ad libitum throughout the in-life portion of the study. Water was available ad libitum. There were no known contaminants in the food or water that interfered with this study.

Animal Selection and Fasting—Animals to be used on test were selected based on overall health and acclimation to caging. Oral arm was be fasted overnight.

Justification—Studies using common mammalian laboratory animals such as mice, rats, dogs, and monkeys are essential and routinely used for the evaluation of the pharmacokinetic characteristics of new chemical entities. The number of animals in each group is the minimum number needed for the assessment of variability between test animals.

EXPERIMENTAL DESIGN—Four Cynomolgus Monkeys were used in this study.

| Group | No. of Animals Male | No. of Animals Female | Test Article | Dose Level* (mg/kg) | Dose Conc* (mg/mL) | Dose Volume (mL/kg) | Vehicle** | Dosing Route | Collect |
|---|---|---|---|---|---|---|---|---|---|
| 1 | 1 | 0 | Dex[a] &Compound 101 | 1 each compound 4 each compound | 1each compound 4 each compound | 1 each compound | H2O | PO, BID (12 H) | Plasma, urine |
| | | | Quinidine | 0 | 0 | 1(Vehicle blank) | DMI:ETOH:PG | | |
| 2 | 1 | 0 | Dex[a] &Compound 101 | 1 each compound | 1 each compound | 1 | H2O | PO, BID (12 H) | Plasma, urine |
| | | | Quinidine | 0.5 | 0.5 | 1 | DMI:ETOH:PG | | |
| 3 | 1 | 0 | Dex[a] &Compound 101 | 1 each compound | 1 each compound | 1 | H2O | PO, BID (12 H) | Plasma, urine |
| | | | Quinidine | 1.5 | 1.5 | 1 | DMI:ETOH:PG | | |
| 4 | 1 | 0 | Dex[a] &Compound 101 | 1 each compound | 1 each compound | 1 | H2O | PO, BID (12 H) | Plasma, urine |
| | | | Quinidine | 6 | 6 | 1 | DMI:ETOH:PG | | |

[a]"Dex" means dextromethorphan
*Each test article will be dissolved at a concentration of 2 mg/mL and dosed at 1 mg/kg
**The formulation will consist of: 10% dimethyl isosorbide, 15% ethanol, 35% propylene glycol (v:v:v) in D5W Dosing Preparation and Administration—Compound 101 and dextromethorphan were each dissolved in water up to 2 mg/mL. The combination dose was prepared by mixing both by 1:1 to yield a concentration of 1 mg/mL for each compound. The concentration of each compound in the dosing solution was re-confirmed by HPLC. Quinidine was prepared in DMI:EtOH:PG:water (10:15:35:40, v/v/v/v) at 3 mg/mL and dosed separately. The doses were given BID orally with an interval of 12 hours. Dosing volume of the dextromethorphan/Compound 100 mixture was 1 mL/kg. Dosing volume of Quinidine was determined based on the dose each animal was getting. Dose volumes for each test animal was determined based on individual body weight. Body weights were taken on each day of dose administration and were be recorded.

Blood Sample Collection—Blood sampling took place on Day 6 after oral administration of the last dose (Dose 11). Blood (approximately 1 mL) was collected via femoral vein into tubes containing sodium heparin anticoagulant at 0.25, 0.5, 1, 1.5, 2, 3.5, 6 and 8 hours. The plasma was separated via centrifugation and stored in −20° C. before analysis.

Urine Sample Collection—Urine samples in between two doses on Day 5 (for 12 hours between doses 9 and 10) were collected in a plate and quantified by volume. After collection, the urine samples were be stored in −20° C. and then shipped back to client.

Acceptable Time Ranges—Blood samples for each time point were collected within 10% for the time points before the first hour and within ±5 minutes for the time points after 1 hour.

Sample Handling and Storage—Blood was stored on ice, or at approximately 5° C. prior to centrifugation to obtain plasma samples. Centrifugation took place within 30 minutes of blood collection to harvest plasma (maximum volume). Plasma samples were stored on dry ice or at approximately −20° C. until analysis.

Antemortem Observations—During dosing and at the times of blood collections, animals were observed for any clinically relevant abnormalities including food consumption, weight, injection position, activity, or feces and urine, for example.

Sample Analysis—Analyses of plasma samples was conducted by the Bioanalytical Group of Medicilon/MPI Inc. The concentrations of both parent compounds (dextromethorphan and Compound 100) and 2 metabolites (Dextrorphan and Dextrorphan-D3) in plasma & urine were determined using a high performance liquid chromatography/mass spectrometry (HPLC/MS/MS API 3000) method. Dilution using cynomolgus monkey plasma blank were applied if the sample concentration was over the ULOQ of calibration standard curve. The data acquisition and control system was created using Analyst 1.4 software from ABI Inc.

Figure 4:
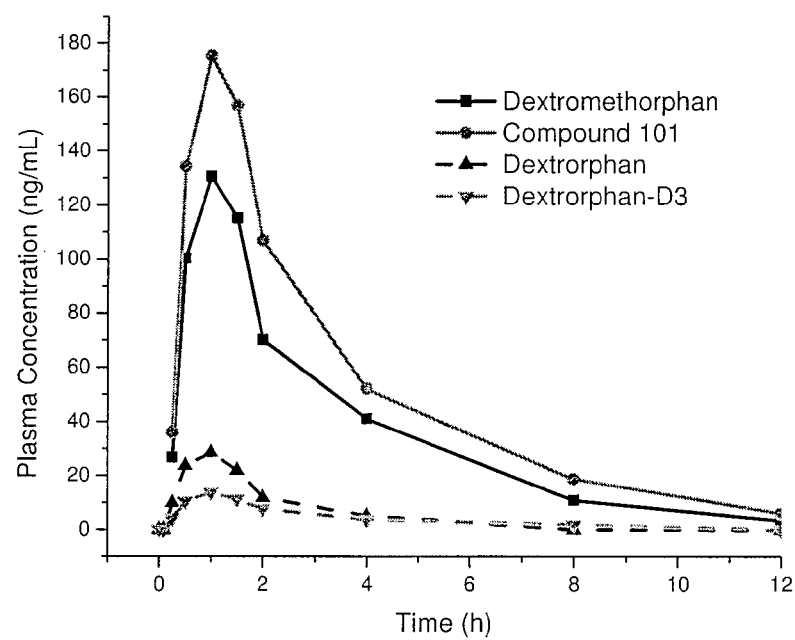
FIG. 4 depicts plasma levels of Compound 101, dextromethorphan, as well as deuterated dextrorphan isotopologues and dextrorphan, in monkeys in the absence of quinidine co-dosing.
Figure 5:
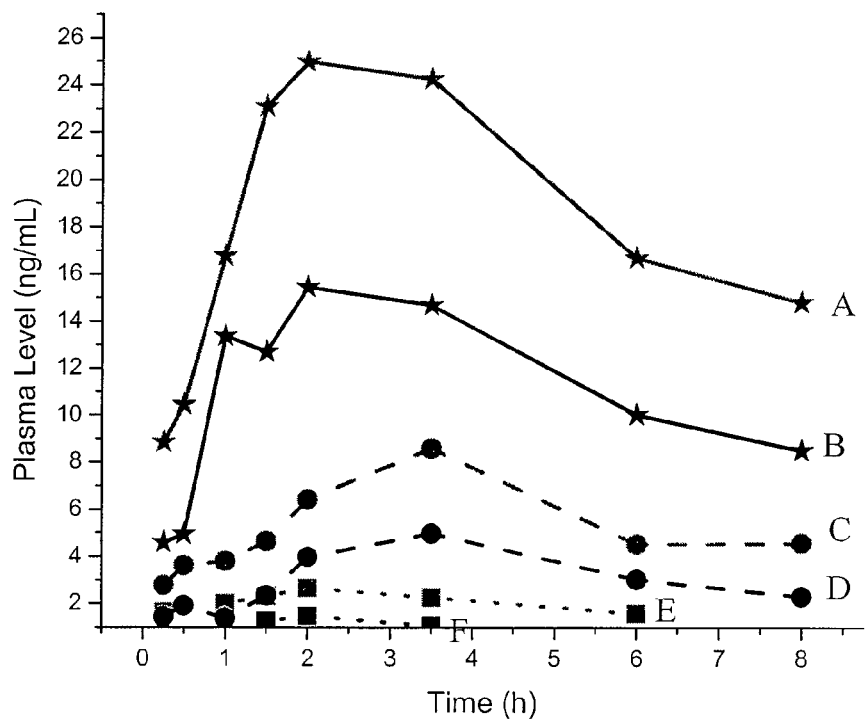
FIG. 5 depicts plasma levels of Compound 101, dextromethorphan, as well as deuterated dextrorphan isotopologues and dextrorphan, in monkeys co-dosed with quinidine.
Figure 6:
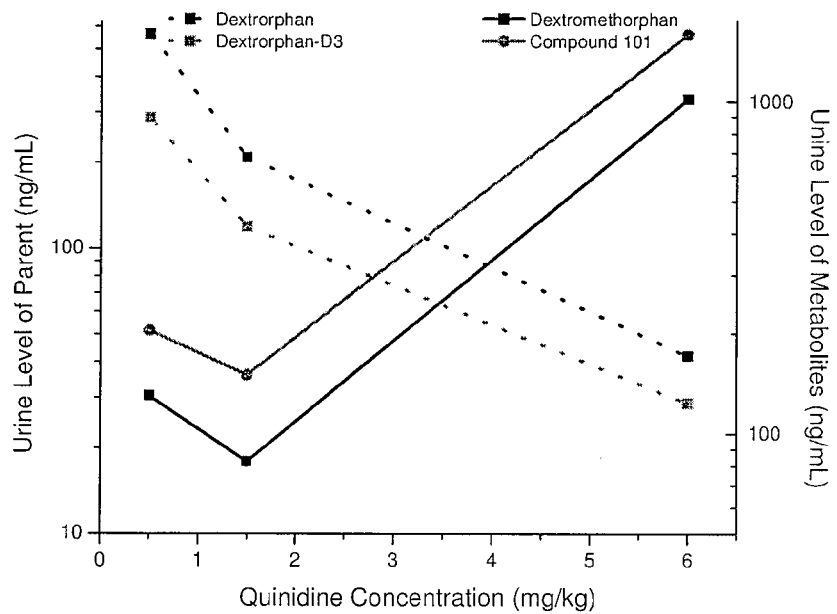
FIG. 6 depicts urine levels of Compound 101, dextromethorphan, as well as deuterated dextrorphan isotopologues and dextrorphan, as a function of quinidine concentration in monkeys

The results are summarized in FIGS. 4, 5, and 6. FIG. 4 depicts the plasma levels of Compound 101 and deuterated dextrorophan compared to dextromethorphan and dextrorphan without quinidine co-administration. FIG. 4 demonstrates that higher plasma concentration levels of Compound 101 are observed compared to dextromethorphan when Compound 101 and dextromethophan are administered to monkeys at the same dose (4 mg). FIG. 4 also shows that metabolism of Compound 101 to deuterated dextrorphan isotopologues is reduced relative to metabolism of dextromethorphan to dextrorphan. As indicated in the Background section of this application, the abuse potential of dextromethorphan are more reliably attributable to dextrorphan, and abuse potential in humans of dextromethorphan metabolism to dextromethorphan. FIG. 4 thus suggests that the compounds of the disclosure may be useful in reducing metabolism of dextromethorphan isotopologues to dextrorphan isotopologues, and thus in reducing the abuse potential of such compounds.

FIG. 5 summarizes codosing data. The results indicate that Compound 101 plasma levels are greater than dextromethorphan plasma levels when each compound is co administered with the same amount of quindine. The relative effect of increasing quinidiine dose has a greater effect on the plasma level of Compound 101 than it has on dextromethorphan.

FIG. 6 depicts urine levels of Compound 101, and dextromethorphan, as well as deuterated dextrorphan isotopologues and dextrorphan as a function of quinidine concentration in monkeys. Compound 101 and dextromethorphan levels are affected by increasing quinidine concentration. At the same quinidine concentration, there is less Compound 101 in the urine than dextromethorphan. Quinidine concentration also affects metabolite levels in the urine. The data indicate that there is less deuterated dextrorphan isotopologues than dextrorphan in the urine for a given quinidine concentration.

Example 5

Radioligand Assay Data Measuring Binding of Compounds to NMDA (PCP) and the Sigma-1 Receptor The assays were run by MDS Pharma Services according to the following references, the contents of which are incorporated herein: Siegel B W, Sreekrishna K and Baron B M (1996) Binding of the radiolabeled glycine site antagonist [3H]MDS 105,519 to homomeric NMDA-NR1a receptors. Eur J Pharmacol. 312(3):357-365; Goldman M E, Jacobson A E, Rice K C and Paul S M (1985); and Differentiation of [.H]phencyclidine and (+)-[.H]SKF-10047 binding sites in rat cerebral cortex. FEBS Lett. 190:333-336. Ganaphthy M E, Prasad P D, Huang W, Seth P, Leibach F H and Ganaphthy V (1999) Molecular and ligand-binding characterization of the s-receptor in the Jurkat human T lymphocyte cell line. J Pharmacol Exp Ther. 289: 251-260.

Assay Methods:

| Glutamate, NMDA, Glycine | |
|---|---|
| Source: | Wistar rat cerebral cortex |
| Ligand: | 0.33 nM [3H] MDL-105519 |
| Vehicle: | 1% DMSO |
| Incubation Time/Temp: | 30 minutes @ 4° C. |
| Incubation Buffer: | 50 mM HEPES, pH 7.7 |
| Non-specific Ligand: | 10 µM MDL-105519 |
| KD: | 6 nM* |
| BMAX: | 3.7 pmole/mg Protein* |
| Specific Binding: | 85%* |
| Quantitation Method: | Radioligand Binding |
| Significance Criteria: | ≥50% of max stimulation or inhibition |

| Glutamate, NMDA, Phencyclidine | |
|---|---|
| Source: | Wistar rat cerebral cortex |
| Ligand: | 4 nM [$^3$H] TCP |
| Vehicle: | 1% DMSO |
| Incubation Time/Temp: | 45 minutes @ 25° C. |
| Incubation Buffer: | 10 mM Tris-HCl, pH 7.4 |
| Non-specific Ligand: | 1 µM Dizolcipine ((+)-MK-801) |

-continued

| Glutamate, NMDA, Phencyclidine | |
|---|---|
| KD: | 8.4 nM* |
| BMAX: | 0.78 pmole/mg Protein* |
| Specific Binding: | 94%* |
| Quantitation Method: | Radioligand Binding |
| Significance Criteria: | ≥50% of max stimulation or inhibition |

| Sigma σ1 | |
|---|---|
| Source: | Human Jurkat cells |
| Ligand: | 8 nM [$^3$H] Haloperidol |
| Vehicle: | 1% DMSO |
| Incubation Time/Temp: | 4 hours @ 25° C. |
| Incubation Buffer: | 5 mM Potassium Phosphate, pH 7.5 |
| Non-specific Ligand: | 10 μM Haloperidol |
| KD: | 5.8 nM* |
| BMAX: | 0.71 pmole/mg Protein* |
| Specific Binding: | 80%* |
| Quantitation Method: | Radioligand Binding |
| Significance Criteria: | ≥50% of max stimulation or inhibition |

*Historical Value

Results.

The binding results are summarized in the following table for Compound 101 compared to dextromethorphan.

| | Dextromethorphan | Compound 101 |
|---|---|---|
| NMDA (PCP) | 2.79 ± 0.39 uM | 3.46 ± 0.34 uM |
| Sigma σ1 | 3.55 ± 0.19 uM | 2.02 ± 0.24 uM |

Without further description, it is believed that one of ordinary skill in the art can, using the preceding description and the illustrative examples, make and utilize the compounds of the present disclosure and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the disclosure. All the patents, journal articles and other documents discussed or cited above are herein incorporated by reference.

The invention claimed is:

1. A method for the treatment of a subject suffering from or susceptible to a disease or condition selected from emotional lability; chronic pain; intractable pain; sexual dysfunction; intractable coughing; dermatitis; and Rett syndrome (RTT), comprising administering to the subject a compound according to formula I:

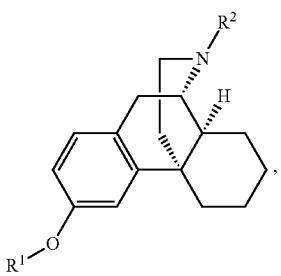

or a pharmaceutically acceptable salt thereof, wherein:
R$^1$ is CD$_3$; and
R$^2$ is CD$_3$.

2. The method of claim 1, wherein any atom not designated as deuterium is present at its natural isotopic abundance.

3. The method according to claim 1 or 2, further comprising administering a second therapeutic agent selected from quinidine and quinidine sulfate.

4. Separate dosage forms of:
(i) a compound of formula I:

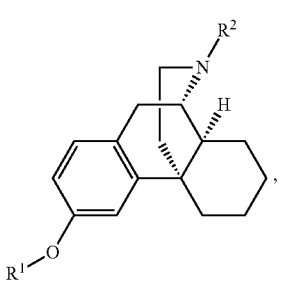

or a pharmaceutically acceptable salt thereof, wherein:
R$^1$ is CD$_3$, and
R$^2$ is CD$_3$;
or a composition comprising a compound of formula I or pharmaceutically acceptable salt thereof formulated for pharmaceutical administration and a pharmaceutically acceptable carrier; and
(ii) a second therapeutic agent selected from quinidine and quinidine sulfate, wherein said compound, pharmaceutically acceptable salt thereof or composition and second therapeutic agent are associated with one another.

5. The separate dosage forms of claim 4, wherein any atom not designated as deuterium is present at its natural isotopic abundance in the compound or pharmaceutically acceptable salt thereof.

6. Separate dosage forms according to claim 4, wherein the second agent is quinidine sulfate.

7. Separate dosage forms according to claim 4 comprising 10-60 mg of the compound of Formula I or pharmaceutically acceptable salt thereof, and 2.5-30 mg quinidine.

* * * * *

UNITED STATES PATENT AND TRADEMARK OFFICE
CERTIFICATE OF CORRECTION

PATENT NO. : 8,748,450 B2
APPLICATION NO. : 13/949499
DATED : June 10, 2014
INVENTOR(S) : Roger Tung It is certified that error appears in the above-identified patent and that said Letters Patent is hereby corrected as shown below:

On the Title Page

Column 1, Page 2, line 51 (Other Publications), please delete "Arkivok," and insert --Arkivoc,--, therefor, Column 2, Page 2, line 24 (Other Publications), please delete "(Methy l enedioxy)" and insert --(Methylenedioxy)--, therefor, Column 2, Page 2, line 49 (Other Publications), please delete "Piperdine" and insert --Piperidine--, therefor, Column 1, Page 3, line 34 (Other Publications), please delete "N-meythlomorphinan" and insert --N-methylmorphinan--, therefor.

Signed and Sealed this
Sixteenth Day of December, 2014

Michelle K. Lee
*Deputy Director of the United States Patent and Trademark Office*